(12) United States Patent
Luk et al.

(10) Patent No.: US 8,569,463 B2
(45) Date of Patent: Oct. 29, 2013

(54) METHOD OF COVALENTLY MODIFYING PROTEINS WITH ORGANIC MOLECULES TO PREVENT AGGREGATION

(75) Inventors: Yan-Yeung Luk, Jamesville, NY (US); DaWei Cui, Syracuse, NY (US); Debjyoti Bandyopadhyay, Syracuse, NY (US); Deepali Prashar, Syracuse, NY (US); Preeti Sejwal, Cranbury, NJ (US); Karen Simon, Fayetteville, NY (US)

(73) Assignee: Syracuse University, Syracuse, NY (US)

( * ) Notice: Subject to any disclaimer, the term of this patent is extended or adjusted under 35 U.S.C. 154(b) by 595 days.

(21) Appl. No.: 12/766,063

(22) Filed: Apr. 23, 2010

(65) Prior Publication Data

US 2010/0273991 A1 Oct. 28, 2010

Related U.S. Application Data

(60) Provisional application No. 61/172,056, filed on Apr. 23, 2009.

(51) Int. Cl.
| | |
|---|---|
| *C07K 16/00* | (2006.01) |
| *C07K 17/00* | (2006.01) |
| *C07K 17/14* | (2006.01) |
| *C07K 1/00* | (2006.01) |
| *C07K 14/00* | (2006.01) |
| *C12P 21/08* | (2006.01) |
| *C08H 1/00* | (2006.01) |

(52) U.S. Cl.
USPC .................. 530/391.1; 530/402; 530/411

(58) Field of Classification Search
USPC ...................... 530/391.1, 402, 411
See application file for complete search history.

(56) References Cited

U.S. PATENT DOCUMENTS

2001/0034333 A1* 10/2001 Kosak .................. 514/44

OTHER PUBLICATIONS

Hou et al. Carbohydr. Res. 2008, 343 (2), 196-210 (published: Feb. 4, 2008).*
Wu et al. J. Am. Chem. Soc. 2007, 129, 16142-16148.*

* cited by examiner

*Primary Examiner* — Fereydoun G Sajjadi
*Assistant Examiner* — Genevieve S Alley
(74) *Attorney, Agent, or Firm* — David L. Nocilly; Bond Schoeneck & King, PLLC

(57) ABSTRACT

A system and method for preventing protein aggregation is developed by covalent modification of proteins with organic molecules that can preserve the native protein folding. Proteins are covalently modified with sugar alcohols or cyclodextrins (organic Kosmotropes) or other small molecule drugs by water-driven bioorganic reactions in water. In the water-driven bioorganic reactions, the reagent is stable in water and can modify lysine residues or cysteine residue of a protein at physiological conditions with high yield and fast rate. Proteins and antibodies will be modified by non-natural sugar alcohols. As a result, the efficacy of protein drugs (reduction in aggregation and enzymatic degradation, and increase in blood stream life time) may be improved.

15 Claims, 34 Drawing Sheets

Squarate linked with sugar alcohols cyclic squarate linked with sugar alcohol

METHOD OF COVALENTLY MODIFYING PROTEINS WITH ORGANIC MOLECULES TO PREVENT AGGREGATION

CROSS-REFERENCE TO RELATED APPLICATION

The present application claims priority to U.S. Provisional Application No. 61/172,056, filed on Apr. 23, 2009.

TECHNICAL FIELD

Embodiments of the present invention relate generally to processes for modifying proteins, and more specifically to methods to prevent protein aggregation.

BACKGROUND OF THE INVENTION

Since the launch of recombinant insulin nearly three decades ago, the protein therapeutics market has boomed to a multibillion industry totaling to $63 billion in 2007 worldwide ($39 billion in U.S. alone), and is projected to reach $87 billion in 2010. Amidst the great therapeutic potential of peptide or protein-based drugs, 96% of all drug candidates have been abandoned during preclinical or clinical development due to solubility or aggregation issues. Though it may proceed through different pathways, aggregation can possibly occur during any of the multiple stages of protein drug processing which may include fermentation, purification, formulation, and even storage—conditions that would subject the proteins under stress or in its non-native environment. Apart from potential decrease in efficacy, and reduced bioavailability, aggregation of protein therapeutics can be toxic leading to serious, detrimental effects such as renal failure and/or immunogenicity. In 2006, a catastrophic example was reported when healthy participants in a clinical trial for a monoclonal antibody drug aimed to boost T cells in the immune system suffered several severe side effects including vomiting, pain, and extreme swelling when the candidate drug was administrated. Despite prior testing showing no ill effects for mice and rats, the response of the human subjects to the synthetic antibody can still be life threatening.

One of the most used strategies in improving the pharmacokinetic property of protein drugs is by polyethylene glycol attachment (PEGylation). A highly flexible, and soluble polymer, PEG has been widely recognized and proven to be an acceptable chemical modification to reduce immunogenicity and aggregation in the protein therapeutics industry. Although PEGylation reduces protein aggregation by blocking undesired contacts with other proteins, large poly(ethylene glycol)s are used, m.w. between 2,000 to 30,000, which is of comparable size of the protein itself. Thus, the mechanism appears to be random large blocking instead of site selective blocking. This approach may suffer from the disadvantage of reducing the drug's specific activity by also blocking the active sites of the modified proteins. Furthermore, the size of the modified protein may vary due to molecular weight variation of the PEG.

Immunoglobulins (IgG) have been routinely isolated from mammalian sera for both diagnostic and therapeutic purposes. Polyclonal antibodies for example, are employed as ligands in immunoaffinity columns or as labeling agents to identify or quantify molecules in various assays such as enzyme-linked immunsorbent assay (ELISA), Western Blot, etc. Immunoglobulin therapy was first introduced in the early 1950's to treat patients who do not produce sufficient antibodies of their own by administering immunoglobulins intramuscularly. Protection from specific diseases or viruses has also been facilitated by hyperimmune IgG infusion. Due to the complex matrix of sera, and the heterogeneity of the size and charge of polyclonal IgG, conventional purification methods by precipitation with inorganic salts or alcohol, electrophoresis, gel permeation and immunoaffinity chromatography can be challenging for large scale IgG isolation.

Protein A from *Staphylococcus aureus* has been widely used in isolating IgG from mammalian sera. Due to its high affinity to the Fc domain of antibodies, Protein A can selectively isolate immunoglobulins from sera or any body fluids rapidly. Since Protein A isolation involves laborious and expensive procedures, supports immobilizing Protein A have been conventionally used for large scale protein purification to maximize the use of Protein A. Protein A immobilized on sepharose and sephacryl gels are now commercially available and are popularly used to isolate IgG's. However, leaching of protein A and hence contaminating the IgG isolates have been noted on sepharose gels. On the other hand, activation of sephacryl gels involves the use of toxic agents. A compromise between yield and purity has always been a problem with IgG isolation

SUMMARY OF THE INVENTION

It is an object of the present invention to prevent protein aggregation by covalently modifying proteins with organic molecules that can preserve the native protein folding—a class of molecules call "organic Kosmotropes". In one aspect of this embodiment, proteins will be covalently modified with sugar alcohols (organic Kosmotropes) by water-driven bioorganic reactions in water. In the water-driven bioorganic reactions, the reagent is stable in water and can modify lysine residues of a protein at physiological conditions with high yield and fast rate. These reagents have been found to be highly superior to existing reagents such as N-hydroxysuccinimide (NHS)-activated carboxylic acids that have an undesirable rate of hydrolysis that complete with the protein modification reaction. Moreover, lysine residues cause more protein aggregation, and can be modified with organic Kosmotropes, than by hydrophobic amino acid residues. In another aspect herein, model proteins and antibodies are modified by non-natural sugar alcohols (alditols) using our new reaction and characterized by Matrix assisted laser desorption ionization mass spectroscopy (MALDI).

It is a further object of the present invention to develop a novel porous hydrogel laden with specific active transferase that efficiently glycosylates peptides or proteins with natural sugars.

It is another object of the present invention to provide a Protein A-laden porous hydrogel to purify and isolate immunoglobulin protein drugs from mammalian sera. This protein-laden porous hydrogel is reusable and affords enhanced enzymatic activity relative to that by non-porous hydrogel. Protein purification methods are provided that specifically utilize the molecules modified on the protein (sugar and non-natural sugar alcohols). Characterization of reduced aggregation and increased thermal stability of modified protein is measured by dynamic light scattering, size exclusion columns and circular dichroism.

BRIEF DESCRIPTION OF THE DRAWINGS

Embodiments of the present invention will be more fully understood and appreciated by reading the following Detailed Description in conjunction with the accompanying drawings, in which.

DETAILED DESCRIPTION

In one embodiment herein, three proteins are glycosylated and/or modified with non-natural sugar alcohols. The thermostability and aggregation properties of the proteins are measured and evaluated. The three proteins include (a) lysozyme, (b) a monoclonal antibody specific to the pilin of *Pseudomonas aeruginosa*, and (c) erythropoeitin. Lysozyme is used as a model protein to test reactivity of the bioorganic reaction.

Lysozyme possesses a readily assessable crystal structure, which enables the effect of modification on the crystal structure to be assessed.

The monoclonal antibody binds to the C-terminus region of pilin on *P. aeruginosa* and thus blocks the initial step of adhering the bacteria to the host epithelium. Functioning as an anti-adhesin, this anti-pilin monoclonal antibody counteracts the infections brought about by *P. aeruginosa* which includes respiratory tract infections in cancer, cystic fibrosis, and intensive care patients.

Erythropoietin (Epo) is a regulatory glycoprotein that stimulates the proliferation, differentiation of erythroid cells into mature blood cells. Recombinant Epo has been used in the treatment of anemia from chronic kidney disease, and of complications from AIDS and cancer therapies. Glycosylation of Epo has been proven to improve protein stability, but also reduced the specific activity. Amgen INC, for example, has developed a hyperglycosylated Epo, Aranesp®, engineered to contain two additional N-glycosylation sites, resulted in an increase in serum half-life by threefold, but also reduced in vitro binding by fourfold. Thus, modification that would maintain both the structure and functions of the protein are highly desired.

Immobilizing small organic molecules known to stabilize protein folding (named as Kosmotropes) can also resist protein adsorption, mammalian cell adhesion and biofilm formation on surfaces. Specifically, mannitol-terminated surfaces have shown superior anti-fouling competence (4 times longer) than oligo(ethylene glycol)-terminated surfaces.

Figure 1:
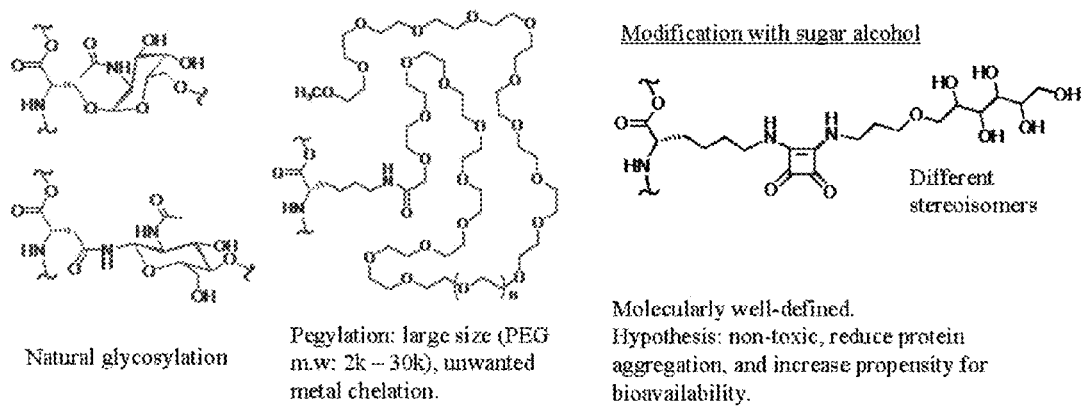
FIG. 1 is a schematic diagram showing protein modification by natural glycosylation, pegylation and covalent modifying protein with sugar alcohols using different stereoisomers.

Reference is hereby made to FIG. 1, which shows (a) natural glycosylation, (b) pegylation and (c) modification with sugar alcohol. By modifying protein with non-natural sugar alcohol, protein aggregation is reduced and blood stream life time is increased. Sugar alcohols derived from hexoses are called alditols, which are usually non-toxics and not recognized by the biological system. For example, a large quantity of mannitol has been used as additives to open up blood brain barrier during brain surgery. Thus, modifying protein with alditiols retains the protein drug benign to the patients. Furthermore, alditols have the same small size as sugars, and thus do not inherit the large size needed for poly (ethylene glycol).

Figure 2:
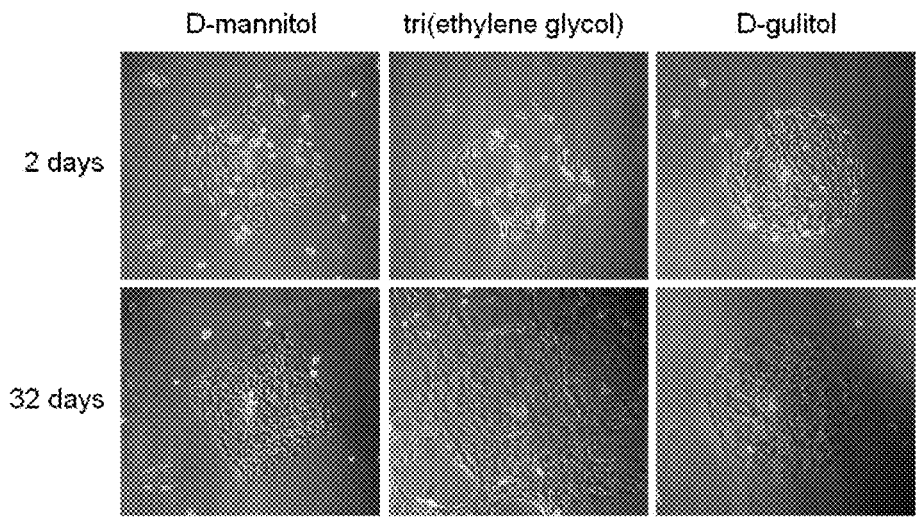
FIG. 2 is a set of micrographs of mammalian cells (3T3 Swiss fibroblasts) confined on methyl-terminated SAMs surrounded by either D-mannitol, D-gulitol or tri(ethylene glycol)-terminated SAMs.
Figure 3:
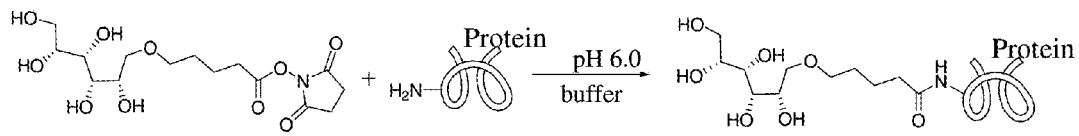
FIG. 3 is a diagram showing the coupling of protein to alditol terminated with acid.

Ions or small molecules that stabilize the native structures of proteins are classified as Kosmotropes. Covalent modification of proteins with organic Komotropes using bioorganic reactions is provided. Modification of proteins with sugar alcohols via bioorganic reactions prevent protein dimerization. Surfaces presenting organic Kosmotropes successfully resist biofouling. For example, D-mannitol-terminated self-assemble monolayers resists mammalian cell adhesion and biofilm formation for about 24 days, whereas tri(ethylene glycols)-terminated SAMs resisted for only 6 days. Reference is made to FIG. 2, which shows that surfaces supported with either D-mannitol or D-gulitol-terminated SAMs resist 3T3 cell adhesion even after 32 days of culture. In comparison, the mammalian cells were confined on methyl-terminated SAMs surrounded by sugar alcohols, here either D-mannitol or D-gulitol, much longer than on tri(ethylene glycol)-terminated SAMs, As resisting protein adsorption is a pre-requirement for resisting mammalian cell adhesion, this result shows that organic Kosmotrope such as D-mannitol has a high potential to prevent protein-protein interactions. Covalent modification of lysine residues on a protein with different stereoisomers of sugar alcohols or alditols is provided. Reference is made to FIG. 3, which shows coupling of protein to alditol terminated with an acid using the following reagents and conditions: (i) EDC, NHS, MES buffer, pH 6.0, 0.5 h, (ii) Lysozyme, MES buffer. D-gulitol linked with a NHS-activated acid group was synthesized and conjugated with lysine residues on lysozymes.

Figure 4:
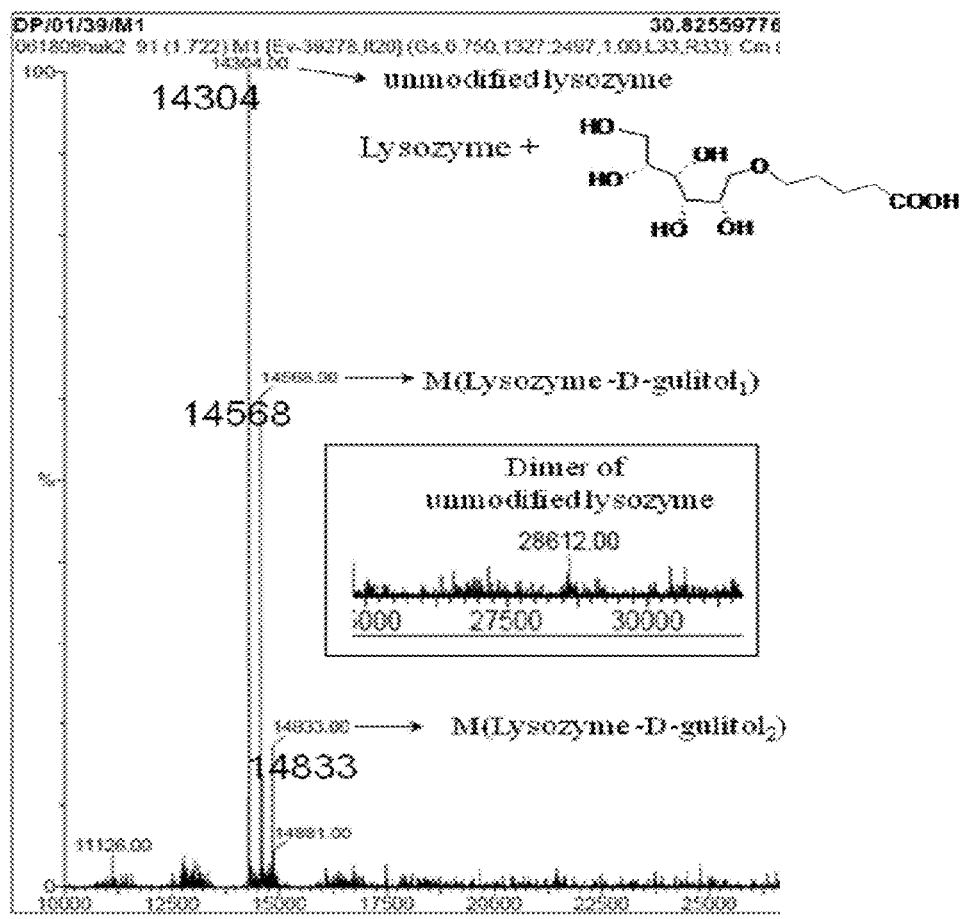
FIG. 4 is mass spectroscopy diagram of covalently modified lysozyme with D-gulitol.

Reference is made to FIG. 4, which shows the mass spectroscopy of monosubstitution and disubstitution of D-gulitol on lysozyme. While the dimer aggregate of unmodified lysozyme is observed, dimer aggregates of modified lysozyme is not observed. Treatment of lysozyme with D-gulitol-terminated acid in presence of coupling reagents EDC and NHS afforded the protein modified with alditol.

The ESI-MS of the dialyzed product, from the lysozyme modification reaction showed that one or two lysine residues were modified on the protein. The mass corresponding to the dimer of unmodified lyozyme was also observed. Such dimer formation is likely due to the aggregation of proteins. On the contrary, mass of dimer was NOT seen for the modified lysozyme as shown in the inset in FIG. 4. Thus, modifying proteins with organic kosmotropes can prevent protein aggregation.

The lysozyme modification was also tested at a pH of 7.8. At this pH, ESI-MS results showed that lysozyme was not modified at all. This result indicated that the protein modification in the presence of EDC and NHS is pH sensitive and occurs in acidic conditions.

Covalent modification of proteins with squarate derivatives by water-driven reactions is provided. Hydrogen bonding capability and high dielectric property of water enable substitution reaction of strained molecules. A class of highly chemoselective reactions between squarate derivatives and amino acid cysteine or peptides with terminal cysteine residue have been found to proceed efficiently in entirely aqueous solution at physiological pH. The reactions are primary promoted by hydrogen bonding in water. Another class of substitution reactions involving the use of water as a solvent have been used to facilitate an efficient synthesis of amino acid-derivatized cyclobutenones. Here the high dielectric constant of water was found to be responsible for the substitution reactions of such strained molecules. The squarate modified proteins and peptides were found to be stable to esterases or cell lysates.

Figure 5:
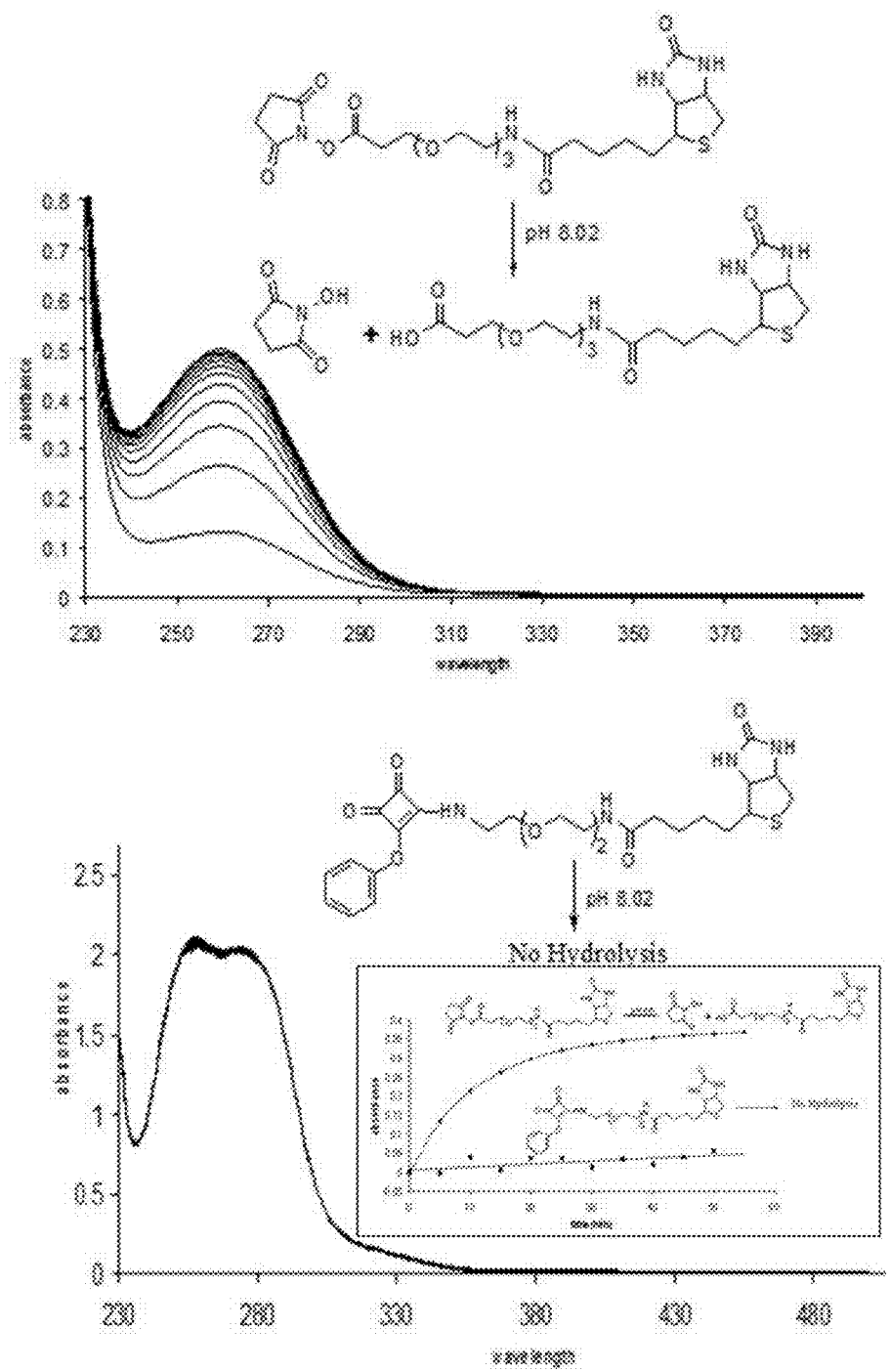
FIG. 5 is a UV-Vis absorption spectra measured at 260 nm data points taken every 5 minutes for an hour.

The stability of squarate conjugation to Biotin is also provided. The stability of PSQ-(PEG)$_2$-Biotin conjugate in aqueous solution was determined by UV-Vis spectroscopy and compared to commercially available NHS-(PEG)$_4$-Biotin conjugate. Reference is made to FIG. 5, which shows UV-Vis absorption spectra measured at 260 nm data points taken every 5 minutes for an hour. The increase in absorption for NHS-(PEG)$_4$-biotin is due to an increase in concentration of release of N-hydroxysuccinimide (molar absorptivity 8.2× 10$^3$ M$^{-1}$ cm$^{-1}$ at 260 nm) that is due to hydrolysis whereas at the same pH no change is observed in PSQ-(PEG)$_2$-biotin absorption spectra. The PSQ-(PEG)$_2$-biotin conjugate was also stable against hydrolysis at neutral pH for at least a week. No detectable hydrolysis was observed in the PSQ-(PEG)$_2$-Biotin solution kept at room temperature for a week whereas the commercially available NHS-(PEG)$_4$-biotin conjugate was rendered completely inactive due to hydrolysis within an hour in aqueous solution. In the inset of FIG. 5, absorption versus time plot shows the kinetics of the hydrolysis of PSQ-(PEG)$_2$-Biotin and stability of NHS-(PEG)$_4$-Biotin. Comparing these results, modifying proteins using squarate chemistry is more reliable than using NHS-activated carboxylic acids because hydrolysis of NHS-activated carboxylic acids competes with the coupling reactions.

Figure 6:
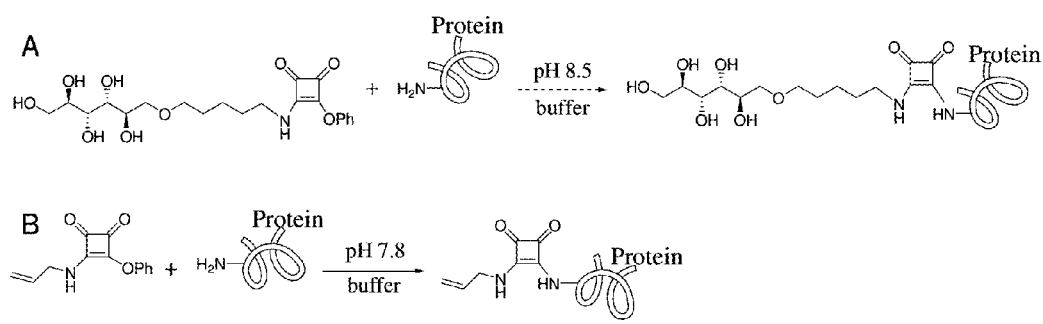
FIG. 6 is a diagram showing lysine residues modified with squarate derivates.
Figure 7:
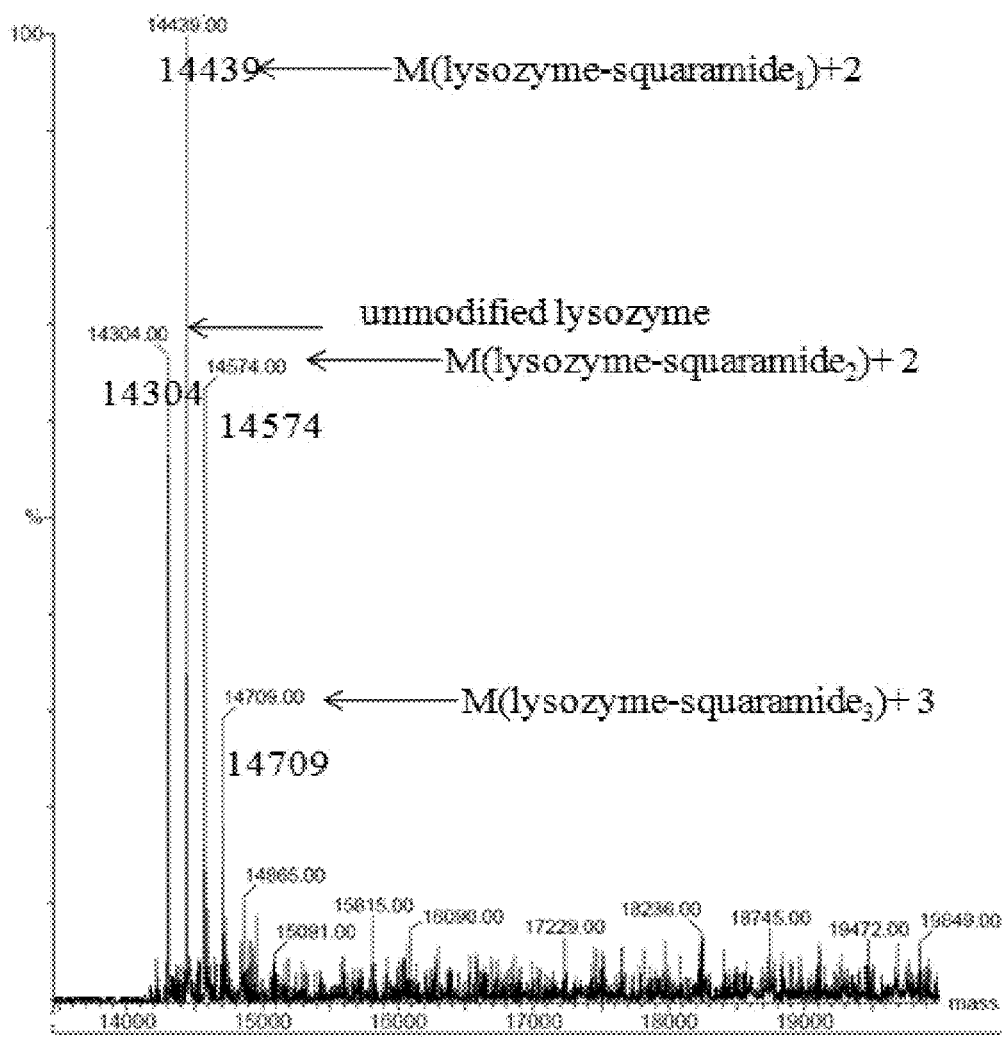
FIG. 7 is an ESI-MS spectra of covalently modified lysozyme with allyl phenoxy squarate.

Reference is made to FIG. 6, which demonstrates a model reaction using allyl phenoxy squarate for protein (lysozyme)

modification in PBS buffer, pH of 7.8. Reference is made to FIG. 7, which shows ESI-MS spectra of the product of lysozyme modified with squarate wherein four lysine residues got modified with allyl phenoxy squarate. This suggests that squarate derivatives can be used to carry out protein modification efficiently when the squarate reagents are completely stable in water.

In the method of covalent modification of proteins with sugar alcohols by organic reaction in water, a water-driven reaction was carried out at a neutral pH for conjugating molecules with selected cysteine in a peptide or a protein and the reaction was driven the dielectric constant of the water solvent. The proteins were modified using two chemistries.

The first chemistry involves the use of N-hydroxysuccinimide (NHS) and 1-ethyl-3-(3-dimethylaminopropyl)carbodiimide hydrochloride) (EDC) to couple acid group on sugar alchohol and lysine residue on a protein as shown in FIG. 3. The second chemistry involves the use of a water-driven reaction to modify lysine residues of proteins with Kosmotrope molecules derivatived with cyclobutenones (squarate moiety) as shown in FIG. 6. This water-driven reaction is carried out at a basic pH of 7.8. At this pH, there is no observable hydrolysis of the squarate reagent. The water-driven reaction overcomes a key challenge in protein modification using NHS/EDC coupling method, which is the propensity of NHS-activated carboxylic to be hydrolyzed by the water molecules. Since the yield of modification was not consistent in every run of modification, a high concentration of NHS-activated carboxylic acids was used to overcome this. This could result in excessive modification of the lysine residues in the protein and may modify potentially important lysine residue in the active site for enzymatic activity. Squarate derivatives are stable in water as shown in FIG. 5 and they are still highly reactive at pH 7.8 for modifying the lysine residues of proteins as shown in FIGS. 6 and 7.

Figure 8:
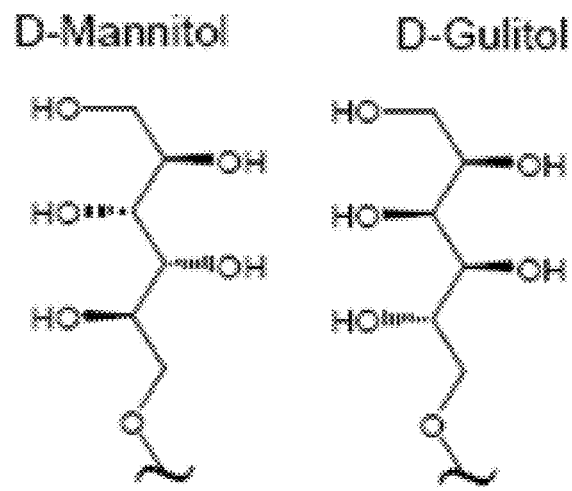
FIG. 8 is a diagram showing structures of organic kosmotropes to be covalently attached to proteins.

Reference is made to FIG. 8 wherein 2 sugar alcohols, mannitol, and gulitol are incorporated with squarate, and lysozyme, erythropoeitin protein, and a monoclonal antibody (specific for the pilin on *Pseudomonas aeruginosa*) are modified with these molecules.

Figure 9:
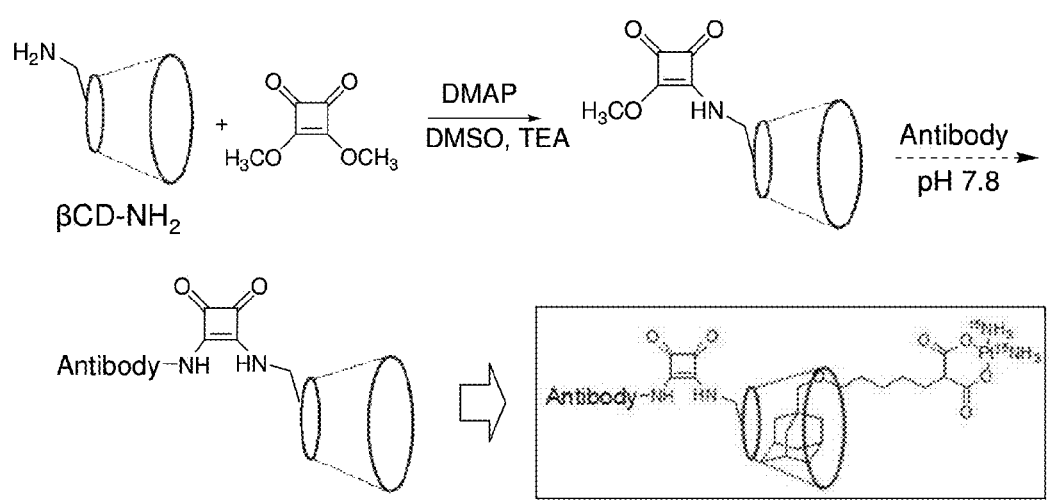
FIG. 9 is a schematic diagram showing modifying antibodies with BCD using squarate chemistry for both reduction of protein aggregation and noncovalent drug loading.

In a further aspect herein, modification of protein with β-cyclodextrin for non-covalent drug loading on proteins is provided. Cyclodextrins (CD) are cyclic oligo sugars that have relatively hydrophobic cores, which can bind a range of non-toxic hydrophobic molecules (such as adamantane and 1-borneol) to form non-covalent inclusion complexes. Reference is made to the insert in FIG. 9, which shows covalently modified proteins with cyclodextrins using squarate chemistry. As sugars in general stabilize protein structure, covalently attaching CDs to proteins reduce their aggregation in solution. Adding CD into solution help prevent protein aggregation and aid in protein refolding. Additionally, CD-modified protein is non-covalently loaded with drugs as shown in FIG. 9. βCD has been known to increase the solubility, bioavailability and stability of hydrophobic drugs. Successfully prepared βCD derivatized with monosquarate moiety is provided having an observed mass of: 1266.37495; and an expected mass of: 1266.37536. This strategy provides a multiple drug action with reduced dosage. The protein can also function as a specific ligand for targeted drug delivery. This is beneficial in modifying anticancer drugs carboplatin and antimicrobial brominated furanones with adamantane onto βCD-modified proteins. Further uses include the use of such drugs for tumor cells.

Figure 10:
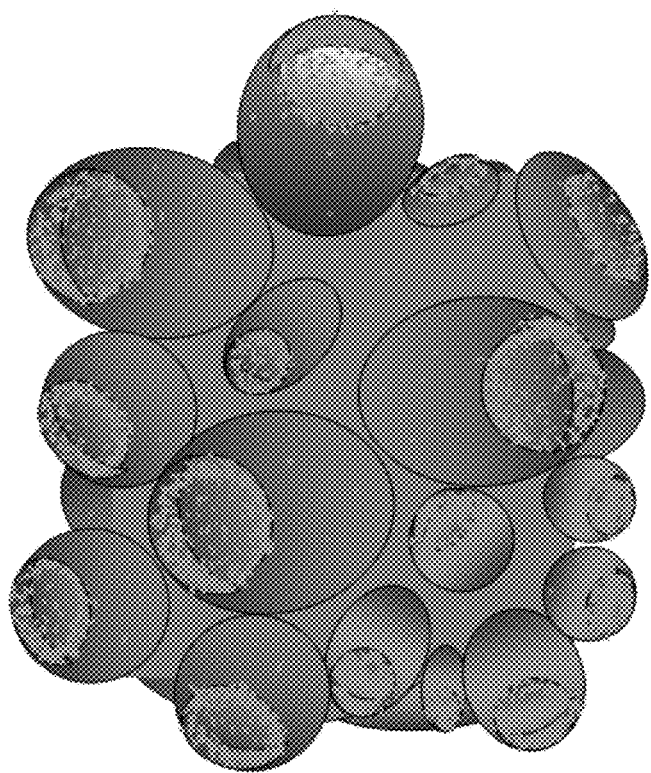
FIG. 10 is a schematic diagram of a hydrogel with protein immobilized on preferred locations.
Figure 11:
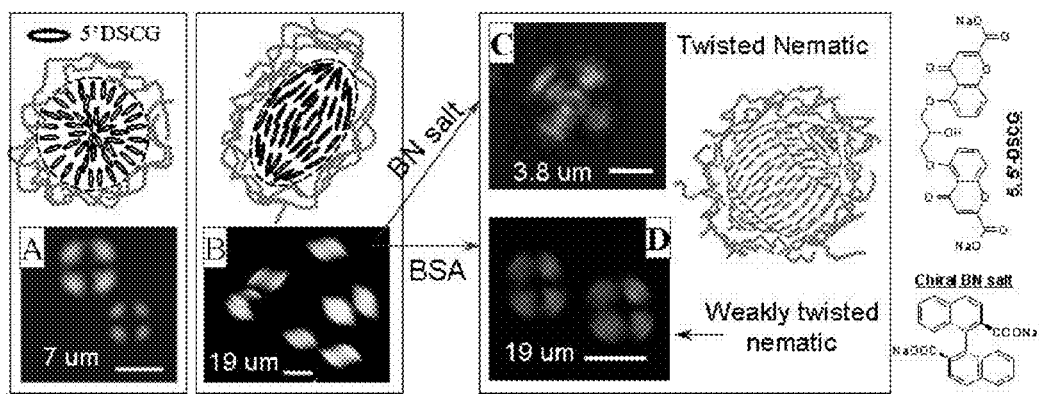
FIG. 11 is a set of images under crossed polars and schemes of water-in-water emulsions.

In a further embodiment herein, covalent enzyme immobilization and protein stabilization in hydrogels based on water-in-water emulsions is provided. In one aspect, water-in-water emulsion of chromonic liquid crystals is provided. Reference is made to FIG. 10, which shows a hydrogen with protein immobilized on preferred locations. A protein-laden hydrogel is made as a water-in-water emulsion as shown in FIG. 11 wherein droplets of water-solvated liquid crystal—disodium cromoglycate (DSCG) are stabilized from coalescence in water by the presence of certain water-soluble polymers (polyacrylamides and polyols). Traditional water-in-water emulsions involve having different biopolymers preferentially partition with its own type and forming different phases in the common solvent—water. In contrast, provided herein are small molecules (DSCG) that can also exhibit water-in-water emulsion phenomena. The orientation of the liquid crystals (DSCG molecules) in the droplets is controlled by the chemistry of the polymer (FIGS. 11A & B) and can respond to the presence of chiral additives or proteins giving rise to novel chiral droplets (FIGS. 11C &D), providing a fertile ground for new studies in soft condensed matter. The mechanism for stabilizing the emulsion in the system herein is fundamentally different from the traditional W/W emulsion. Only thermodynamic incompatibility of different biopolymers is responsible for the traditional water-in-water emulsion.

FIG. 11 shows images under crossed polars and schemes of fundamentally new water-in-water emulsion. FIG. 11A shows 10.9 wt % polyvinyl alcohol & 6.4 wt % DSCG; DSCG liquid crystals align perpendicular to the droplet surface. FIG. 11B shows 12 wt % polyacrylamide & 8 wt % DSCG, DSCG aligns parallel to droplet surface. FIG. 11C shows 4 wt % binaphthyl (BN) salt and FIG. 11D shows 0.5 wt % of BSA protein added into the system of FIG. 11B, the liquid crystal adopts onion configuration (cholesteric phase) with twisting orientation of each layer of molecules for systems in FIG. 11C and FIG. 11D.

In addition to the incompatibility of different types of molecular interactions, including dispersion forces (pi-stacking), hydrogen bonding and salt bridges entirely solvated in water, multivalent binding between the polymer and DSCG molecules on the surfaces of the droplets also arise to prevent coalescence and Ostwald ripening of the droplets. This polymer coating on liquid crystal droplets is fundamentally new and is extremely useful for working with proteins because the whole system (polymer and DSCG) does not denature proteins. The 3-component (water, DSCG and polyacrylamide) phase diagram shows that the water-in-water emulsion exists with a concentration of DSCG from 3-12 wt %. Previously, it has been shown that high concentration of DSCG (11 wt % in water) in liquid crystal phase does not disrupt the specific binding between antigen and antibody.

Figure 12:
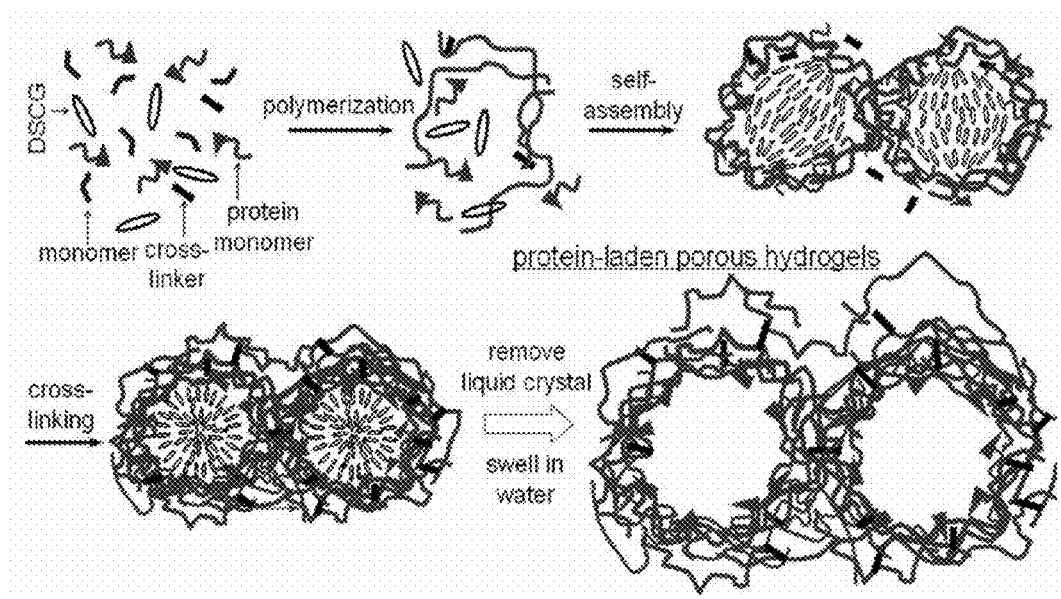
FIG. 12 is a schematic diagram of one-pot fabrication of protein-latent connected hydroshell.
Figure 13:
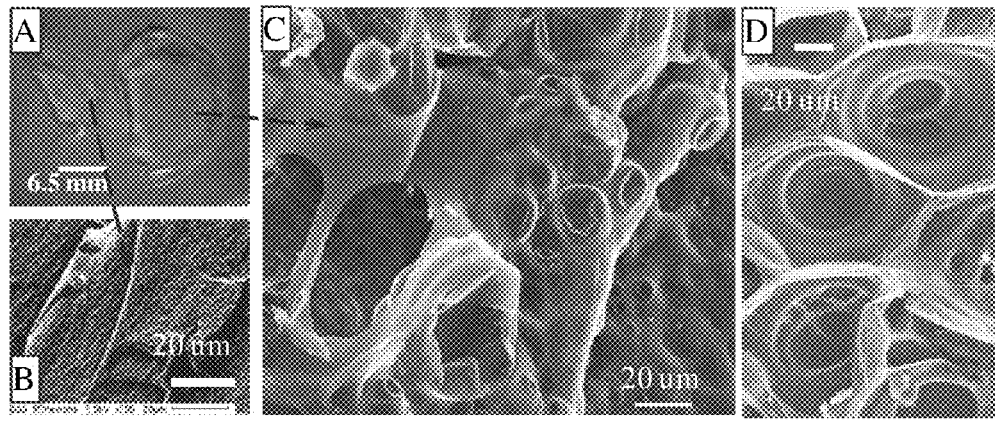
FIG. 13 is a set of micrographs showing swelling of porous and non-porous polyacrylamide hydrogels prepared with and without the presence of DSCG.

In another aspect herein, a method of making a porous hydrogel with immobilized proteins is provided. It is preferable that the proteins are located towards and on the pore surfaces. Methods for making porous hydrogel include but are not limited to using lyotropic liquid crystal assemblies as templates and as polymerizable scaffold for the fabrication of new materials. The method herein includes using water-in-water emulsion as template for making materials and a system to retain the activity of the proteins involved in the synthesis of the materials. A porous hydrogel with shell-like morphology is created by polymerizing and cross-linking the monomers (acrylamide) in situ with the presence of DSCG, in which pores of encapsulated DSCG molecules are coated by a layer of cross-linked polymers. Subsequently, the DSCG molecules can be readily removed from the hydrogel matrix through diffusion out of the gel materials (essentially a dialysis) by soaking the sample in excess of water as shown in FIG. 12. FIG. 12 shows one-pot fabrication of protein-latent connected hydroshell: polymerization of monomers, phase separation forming polymer-dispersed LC droplets, cross-linking the polymer coating on LC droplets, removal of the 5'DSCG molecules through diffusion by soaking the sample in water. Scanning electron microscopy reveals a connected shell structure (instead of a Swiss cheese morphology) in the hydrogel materials in FIG. 13 supporting the notion of polymer coating on the droplets. The pore size ranges from 20-40 µm in diameter, which can facilitate the rapid transport of proteins as well as bacteria (~1 µm) and mammalian cells (10-30 µm). FIG. 13 shows swelling of porous and non-porous polyacrylamide (PAAm) hydrogels prepared with and without the presence of DSCG. The SEM images in FIG. 13 show a PAAm hydrogel prepared with (A) 12 wt % AAm, 1 wt % BIS, 0.4 wt % APS, 0.2 wt % TEMED, (B) without 5'DSCG, (C) with 8 wt % 5'DSCG, and (D) with 8 wt % 5'DSCG and 2 wt % binaphthyl salt.

Many methods have been developed to immobilize proteins on materials. For example, proteins have been immobilized on agarose (a galactose-based polysaccharide), polyacrylonitrile (PAN) membranes, mesoporous silica and other materials via often multiple steps of chemical reactions. Some conjugation methods including disulfide and imine bond formation between protein and solid support are reversible and unstable at certain pH, and thus are less desired methods. The locations of the immobilized protein in materials are often not controlled. Overall, these methods are primarily aimed for biotechnology purposes such as making the enzyme reusable.

Figure 14:
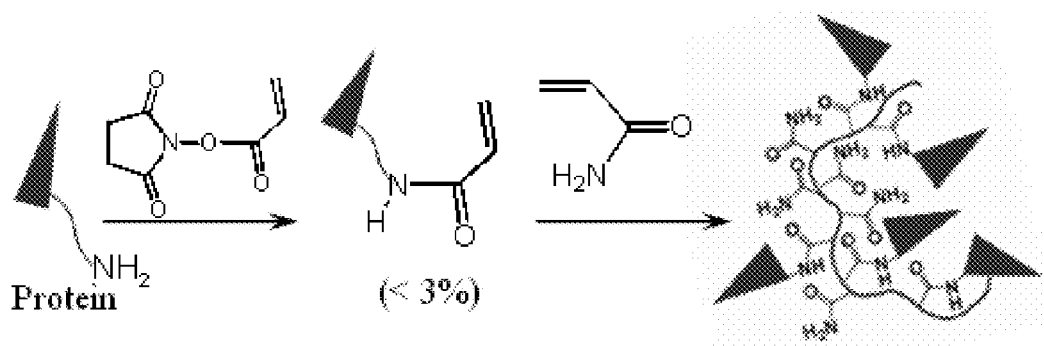
FIG. 14 is a schematic diagram of protein immobilization using the abundant lysine groups on a protein coupled with N-succimidylacrylate in phosphate buffered saline to afford vinyl-modified proteins.
Figure 15:
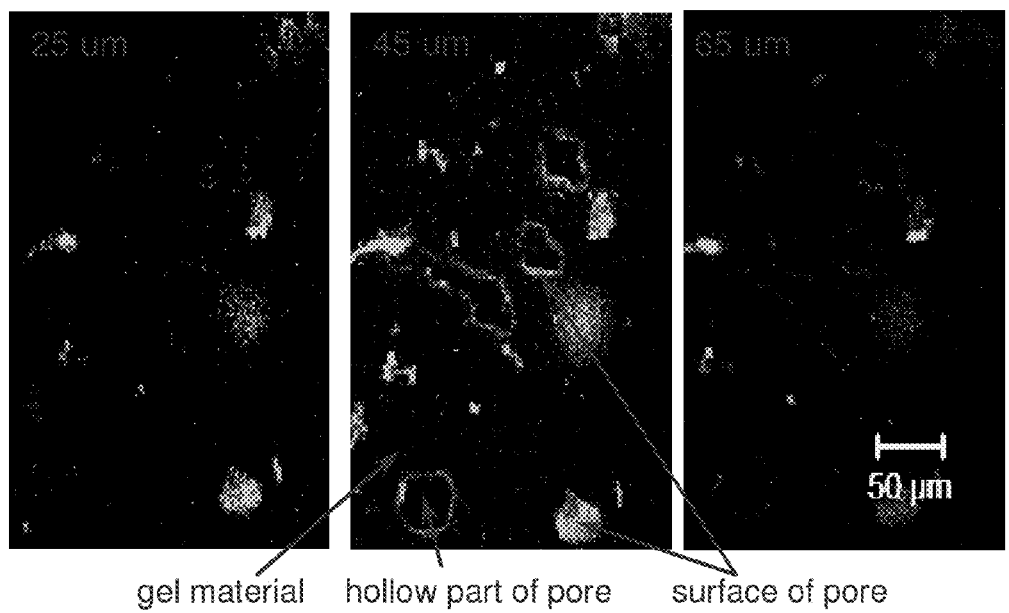
FIG. 15 is a confocal fluorescent image of porous hydrogel made by w/w emulsion and showing the confocal depth.

In another aspect herein, copolymerization of proteins is preferably on the pores. Reference is made to FIG. 14, which shows a protein modified with polymerizable moiety present in the pre-gel solution. The proteins are polymerized into the gel preferably towards and on the surface of the pores that are in contact with the DSCG molecules as shown in FIG. 12. The chemistry for protein immobilization, uses the abundant lysine groups on a protein to coupled with N-succimidylacrylate in phosphate buffered saline (pH 7.4) to afford vinyl-modified proteins as shown in FIG. 14. This acryloyl-modified protein was mixed with other acrylamide monomers (3:97) and DSCG (~8 wt %) in one-pot polymerization and cross-linked to produce protein-laden porous hydrogel. The preferred location of immobilized protein was confirmed by measuring confocal fluorescence of an immobilized fluorescent protein (FITC-tagged avidin). Fluorescent signal was observed only on the surface and the layer of the pores as shown in FIG. 15, which is a conocal fluorescent image of a porous hydrogel made by w/w emulsion. As a control, when the loading of the FITC-tagged avidin is increased from 7450 fold (from 200 nM to 1.49 mM), fluorescent signals are observed in the entire gel materials.

Figure 16:
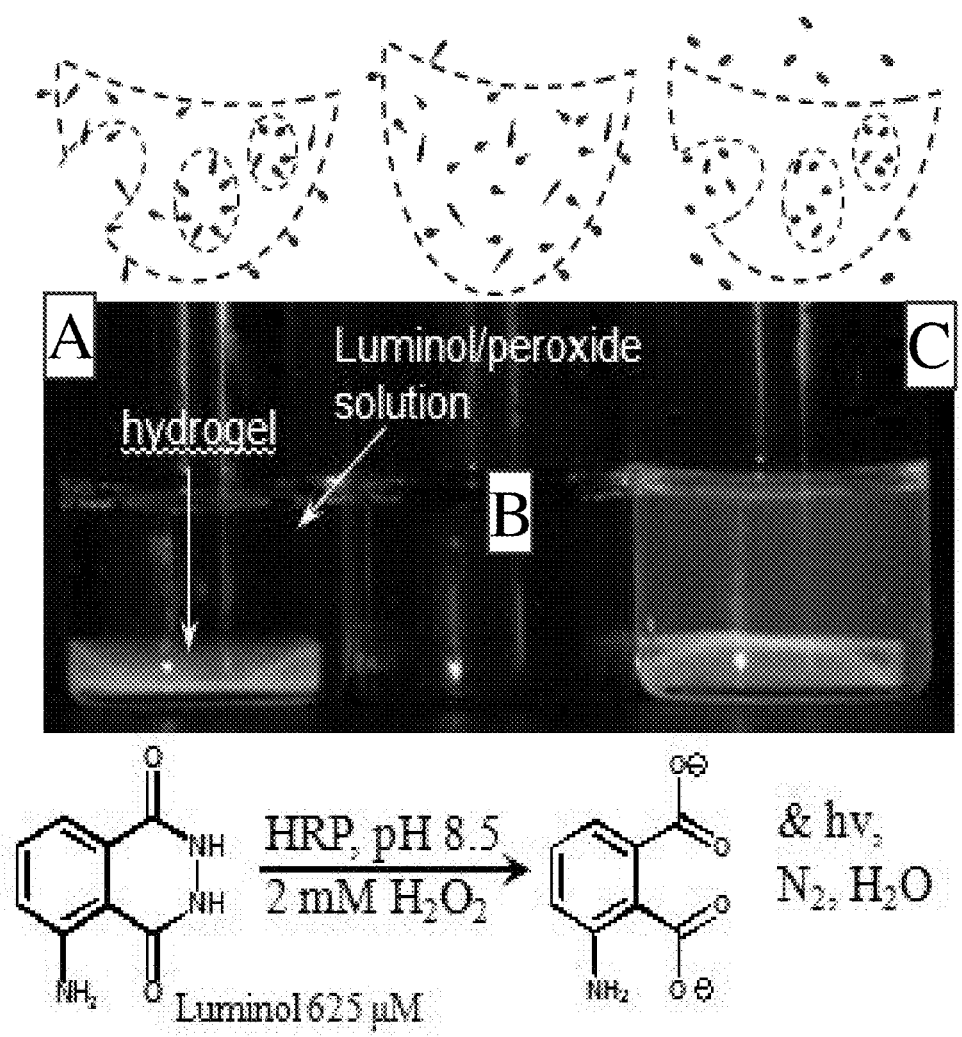
FIG. 16 shows biocatalystsis of luminol reaction by HRP covalently immobilized on porous polyacrylic amide hydrogel (16A), nonporous hydrogel (16B) and by HRP non-covalently absorbed in a porous hydrogel (16C).
Figure 17:
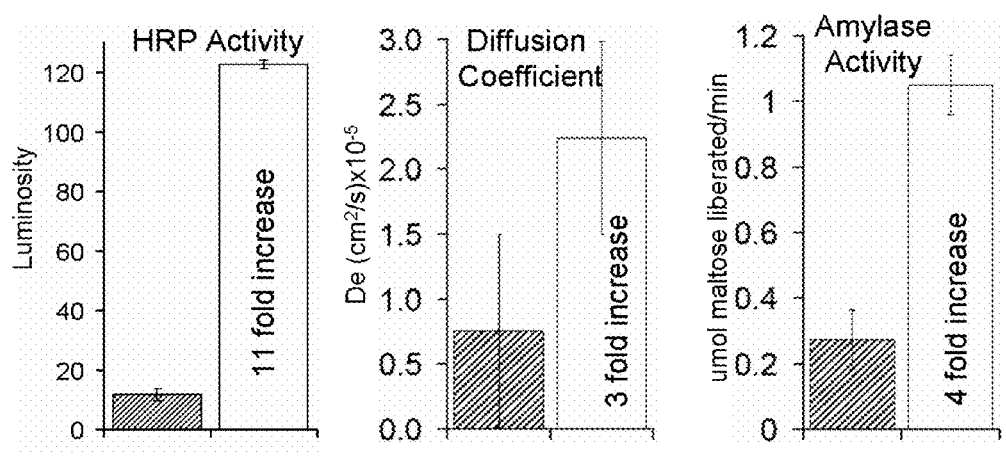
FIG. 17 shows protein activities and diffusion coefficient for non-porous (shaded bar) and porous (white bar) hydrogel.

In a further aspect herein enhanced enzymatic activity of a protein-laden connected hydro-shell is provided. The enzymatic activities of 3 different enzymes (horseradish peroxidase, amylase and aldolase) immobilized on polyacrylamide porous hydrogel prepared in the one-pot method was carried out. (FIG. 10). Horseradish peroxidase (HRP) was used to catalyze a chemiluminescence reaction of luminol dissolved in solution, which generates a visible blue light (424 nm); amylase was used to catalyze the breakdown of polysaccharide (β-cyclodextrin) by hydrolyzing α-1,4-glycosidic linkages, and aldolase (N-Acetylneuraminic acid aldolase, a type I aldolase from *E. Coli*) was used to catalyze the ligation between monosaccharides (mannose) and pyruvates to form sialic acids. Whereas porous HRP-laden hydrogel emits intense blue light as shown in FIG. 16A, the non-porous version show essentially no light emission (FIG. 16B). Porous hydrogel soaked in a solution of free HRP followed by immersion in a luminol solution shows blue light emission in the whole solution shown in FIG. 16C supporting that HRP is covalently immobilized on the hydrogel as in the case of FIG. 16A. The activity of amylase is characterized by a colorimetric assay that depends on the reduction of dinitrosalicylic acid by the anomeric group of enzymatic reaction product (degraded sugar fragments from β-cyclodextrin. The diffusion of bovine serum albumin (BSA) from the hydrogels was characterized by first soaking the hydrogel in a BSA solution followed by immersion in fresh buffer. The diffusion of BSA from hydrogel into the fresh buffer over time is determined through Bradford assay, in which the concentration of BSA in the buffer is measured by the UV absorbance change resulting from the protein reacting with a Coomassie blue dye. FIG. 17 summarizes the quantified enzymatic activities of HRP and amylase, as well as the diffusion coefficient of BSA from porous and non-porous hydrogel. For both HRP and amylase, the enzymatic activities are higher on porous hydrogel than non-porous hydrogel. For HRP, the increase in enzymatic activities in porous over non-porous hydrogel is significantly higher than that of the magnitude in the increase of diffusion coefficient; whereas for amylase, the magnitude in the increase of enzymatic activity is similar to that in diffusion coefficient. This result suggests that diffusion due to porosity alone does not sufficiently account for the increase in enzyme activity on hydrogel. In summary, the enzyme activity is highly retained, and potentially enhanced, on porous hydrogels based on water-in-water emulsions.

Figure 18:
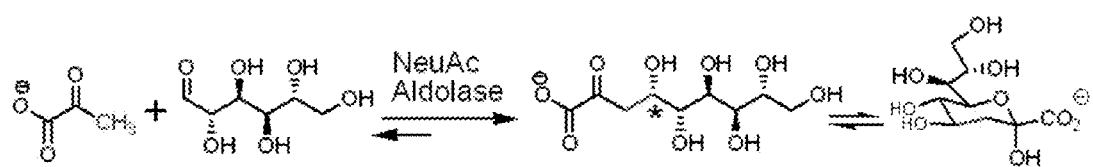
FIG. 18 is a diagram of the activity of aldolase for synthesizing sialic acids.
Figure 19:
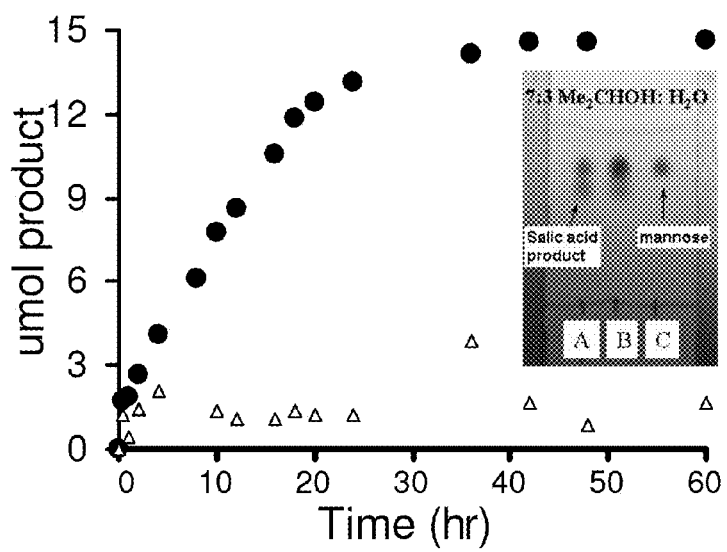
FIG. 19 is a graph showing the amount of sialic acid produced by porous hydrogel with and without immobilized aldolase over time.

The activity of aldolase for synthesizing sialic acids is also provided. This enzymatic reaction makes a carbon-carbon bond instead of breaking one. The pore surfaces of the hydrogel can change the equilibrium between the cyclic and linear form of the mannose substrate, shown in FIG. 18. FIG. 19 shows the amount of sialic acid generated by porous hydrogel laden with aldolase over time by measuring the depletion of one of the substrate, pyruvate. The product, sialic acid, is confirmed by mass spectroscopy and thin layer chromatography. In FIG. 19, the amount of sialic acid produced by porous hydrogel with immobilized aldolase over time is shown by the filled circle and without immobilized aldolase over time is shown by the unfilled triangle. The solution constains 293 mM of mannose and 10 mM of pyruvate in a pH 7.5 PBS buffer. The hydrogel is swelled with pyruvate solution; volume of solution absorbed by the gel is obtained by the different mass between wet and dry weights of the hydrogels. The inset in FIG. 19 shows TLC of the sialic acid product.

Figure 20:
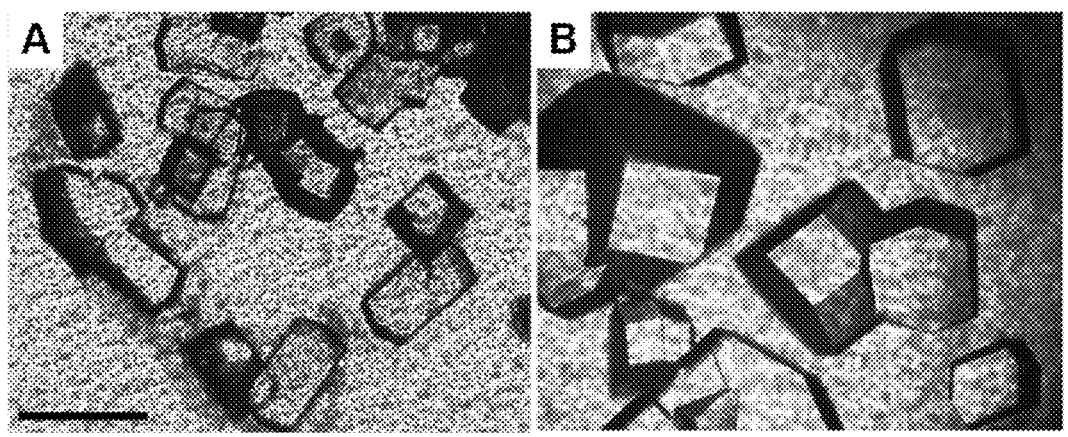
FIG. 20 is a set of micrographs showing lysozyme crystallized using DSCG (20A) and NaCl (20B) in 50 mM sodium acetate buffer (pH 4.5) in hanging droplet methods.

In a further aspect herein, stabilizing and recrystallizing proteins using disodium cromolyn glycate (DSCG) and other dichromonyl molecules is provided. DSCG molecules are non-amphiphilic and stabilize protein structures. For example, at relatively high concentrations in water (above 11 wt %, i.e. 214 mM), DSCG forms liquid crystal phases—so-called "chromonic liquid crystals". Antigen proteins dissolved in this liquid crystal still bind specifically to their corresponding antibodies immobilized on surfaces. Vapor diffusion experiments were performed by hanging a drop of solution containing 2.55 mM lysozyme and 2.73 mM DSCG over a reservoir solution having twice as much concentration of DSCG. Reference is made to FIG. 20A, which shows hexagonal crystals of lysozyme formed after 48 hours using DSCG as a crystallizing agent (2.73 mM). In contrast, in FIG. 20B, in the same crystallization experiment, a much higher concentration of sodium chloride (450 mM) is needed to induce crystal formation of lysozyme. Based on these results, it is believed that DSCG molecules stabilize protein structures and exclude protein from the droplets, which accounts for enhancement of activity of enzymes immobilized on hydrogel made by templated synthesis using water-in-water emulsions.

In a further aspect, a method of glycosylation of peptides and proteins for preventing protein aggregation and increasing bioavailability by heterogeneous biocatalysis is provided. An enzyme-laden porous hydrogel built from water-in-water emulsion is used in this method.

Figure 21:
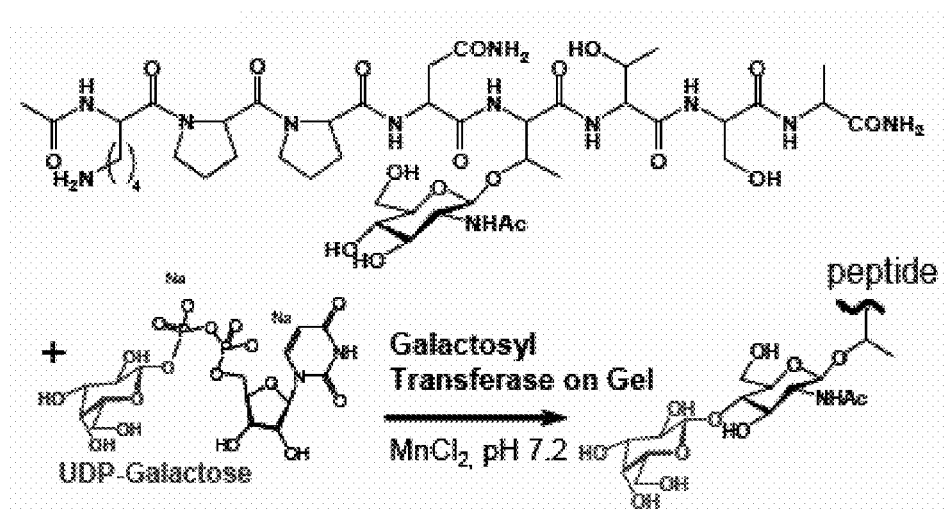
FIG. 21 is a schematic diagram showing glycosylation of peptides by galactosyl transferase on hydrogel.

Reference is made to FIG. 21, which shows enzyme-laden porous hydrogel to glycosylate peptides and proteins, β-1,4galactosyltransferase (b4Gal-T1) and used to catalyze the transfer of galactose from UDP-galactose to a protein-bound or a peptide-bound N-Acetylglucosamine Its functions involve glycosylation of targeted peptide and protein substrates, it also catalyze synthesis of disaccharides. This protein is also found on cell membranes and is believed to function as a cell adhesion molecule. There are ten lysine residues in β4Gal-T1 that are used to modify with acrylic moiety for immobilization. None of these lysine residues are conserved from different animal sources, and thus are unlikely to be involved for enzymatic activity. The enzymatic activity of immobilized β4Gal-T1 on glycosylation of peptides and protein Ovalbumin was measured.

The catalytic activity of β-1,4-galactosyltransferase (β4Gal-T1) immobilized on porous hydrogels was characterized and measuremed. To test the glycosylation by transferase laden hydrogel, β4Gal-T1 was used to glycosylate a peptide as shown in FIG. 21 and Ovalbumin. Ovalbumin has two potential glycosylation sites for β4Gal-T1. The kinetic data ($K_m$ and $V_{max}$) for b4Gal-T1 on both of the two substrates are known and thus the changes in enzymatic activities due to immobilization were measured and the mechanism for the changes is provided. First, the amount of enzyme actually immobilized on the hydrogel by using a "Bradford" assay was measured. This provides the amount of protein that is not immobilized on the hydrogel due to incomplete reaction during the one pot hydrogel fabrication. For example, for aldolase, immobilization yield measured was about 74% of the enzymes on porous hydrogel used by this method. The amount of immobilized protein is obtained by subtracting the diffused enzyme from the total enzyme used in the reaction. The product and the enzyme kinetics of glycosylation of the peptide is measured by liquid chromatography mass spectroscopy. The product of the glycosylation of Ovalbumin is purified by high performance liquid chromatography (HPLC) and characterized by matrix assisted laser desorption/ionization (MALDI), and the enzyme kinetics is assayed by using radiolabelled uridine diphosphate galactose (UDP-galactose).

The reusability of the β4Gal-T1-laden porous hydrogels was evaluated by measuring the activity of the immobilized enzyme after every cycle. This determined how much active enzyme is retained in the hydrogel after every use. The storage condition that preserve the activity of the immobilized enzyme longer is also provided. Proposed storage conditions include (i) lyophilization, and (ii) dehydration via speed vacuum. This provides the basis for a commercial product of heterogeneous biocatalyst that can carry specific enzyme for glycosylation of targeted protein drugs.

The aggregation and thermal stability for modified proteins was evaluated and compared with native proteins. Dynamic light scattering and size exclusion columns were used to characterize the aggregation, and circular dichroism was used to measure the thermal stability of modified proteins. The dynamic light scattering assessed the hydrodynamic radius of particle range from a few nanometers to micrometers, and estimated the shape of the aggregates. Dynamic light scattering was used to measure the shape and critical aggregation concentration for assembly formed by a novel folded surfactant comprised of a β-cyclodextrin head group. To measure protein aggregation, DLS was used to measure the hydrodynamic size of proteins (lysozyme, monoclonal antibody specific for pilin and erythropoietin) covalently modified with mannitol and gulitol with different concentration of a denaturant guanidinium chloride. As aggregate forms by the denatured protein, the size of the aggregates will increase and be characterized by the DLS. To measure small aggregation, such as dimmer formation, high performance size exclusion columns were used to estimate the molecular mass of the protein or aggregate. Thermal stability of modified proteins is characterized as a function of increasing temperature by circular dichroism. As the protein denatures by heat, the circular dichroism signature of the secondary structure from the protein transitions to signature of a random core. The temperature at which protein denature was measured. Modified proteins exhibit less aggregation and higher temperature for denaturation than that by unmodified native proteins.

In a further embodiment herein, methods of protein drug purification by using protein A or phenyl boronic acid are provided. Protein isolation from mammalian serum, body fluids, and cell culture has been an expensive, but indispensable process in clinical diagnosis and drug industry. In a method herein, porous hydrogels based on water-in-water emulsions are utilized to fabricate two new materials that can (1) isolate immunoglobulins from mammalian sera, and (2) isolate stabilized sugar-tethered proteins which we modified as described above. The porous hydrogel based protein isolation tool provided herein is compared to the existing technologies being used in the biopharmaceutical industries.

Figure 22:
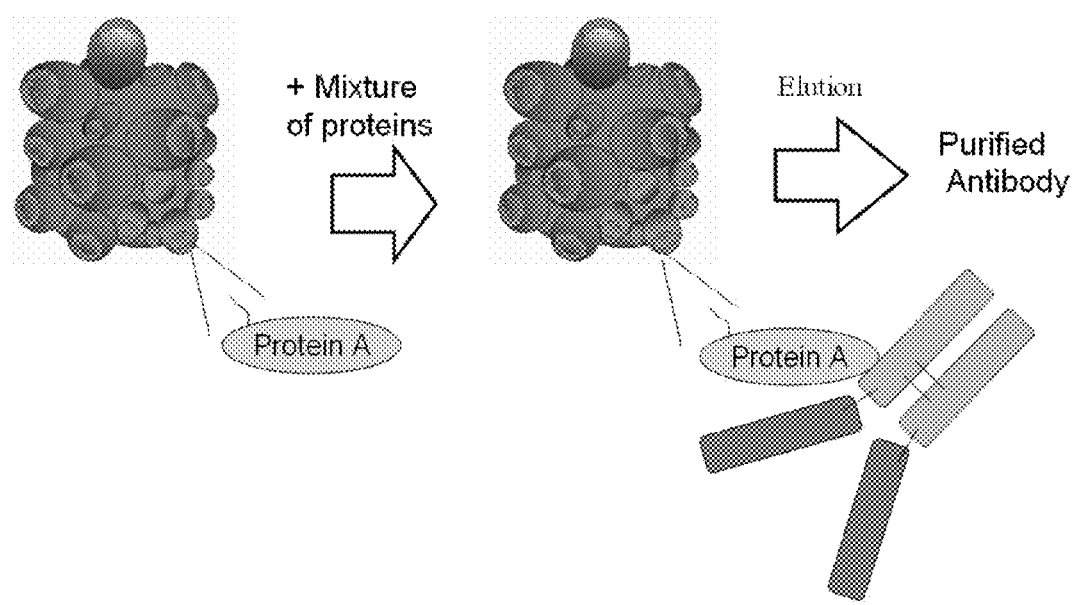
FIG. 22 is a schematic diagram showing antibody purification using Protein-A laden porous hydrogels.

Protein A-laden porous hydrogels for the purification of antibodies IgG isolation by Protein A-laden porous hydrogel were fabricated. immobilize Protein A was immobilized in porous hydrogels and IgG was isolated from commercially-available mammalian sera. Reference is made to FIG. 22, which shows the strategy for antibody purification using Protein-A laden porous hydrogels.

The porous hydrogels based on water-in-water emulsions provided herein are a suitable support for immobilized Protein A. Since immobilized proteins localize on the surface of the pores of these hydrogels, IgG from body fluids can be efficiently isolated by the immobilized Protein A that are exposed on the pore surface of the gels. Furthermore, covalently incorporating acrylamide-derivatized Protein A as a copolymer prevents its leakage during the elution of IgG.

The ability of Protein-A laden porous hydrogels in isolating IgG's from sera was evaluated. To isolate IgG from mammalian sera as well as assess the purity of the isolate, sodium dodecyl sulfate polyacrylamide gel electrophoresis (SDS-PAGE) was used. To determine the binding capacity of the gels, size exclusion high performance liquid chromatography (SE-HPLC) was employed to determine the concentration of isolated IgG. Simultaneously, SE-HPLC can also be used to detect possible contamination of Protein A during elution of bound IgG.

In yet another embodiment, phenyl boronic acid-laden hydrogels to purify glycosylated proteins are provided. Porous hydrogels copolymerized with phenyl boronic acids were used to isolate the proteins modified with sugars (glycosylated proteins) as described above. Boronates, known to form complexes with diol groups, have been employed in chromatography to isolate sugars, glycoproteins and ribonucleotides. Since the molecular weights of the sugars are significantly low compared to the proteins they were coupled to, isolation of the proteins modified with sugars from those that were left unmodified would be challenging using HPLC techniques, and utilizing boronate chromatography would be a more strategic purification technique.

Figure 23:
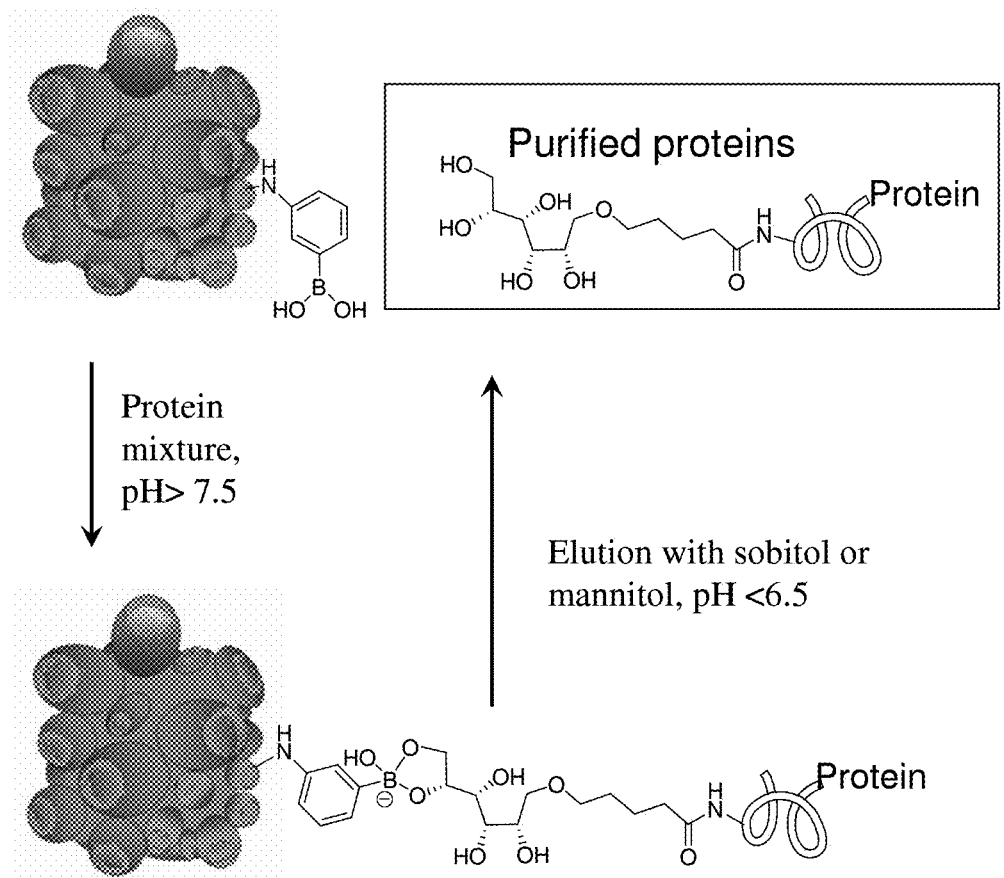
FIG. 23 is a schematic diagram showing purifying glycoslyated proteins using phenyl boronic acid-laden porous hydrogels.

In the method herein, m-acrylamidophenyl boronic acid was copolymerized with acrylamide in porous hydrogels. Reference is made to FIG. 23, which shows the strategy for purifying glycosylated proteins using phenyl boronic acid-laden porous hydrogels. Based on thermodynamic incompatibility, the aromatic moiety of m-acrylamidophenyl boronic acid interacts with the DSCG in the droplet phase, and facilitates its localization on the interface of the water-in-water emulsions-based hydrogel during copolymerization with the porous hydrogel. Exposure to the boronate acids on the surface of the pores then readily interacts with the two hydroxyl groups of the sugar moieties of the glycosylated proteins, thereby facilitating isolation from the unmodified proteins.

To verify whether the phenyl boronic acids were localized on the surface of the pores, the gels were exposed in an aqueous solution of a sugar conjugated with a fluorescein (ex. FITC). Confocal microscopy identified the location of the boronates copolymerized on the gels. To assess the ability of the boronate-laden hydrogels, the isolates were subjected to MALDI for identification and characterization of proteins captured by the boronate-laden porous hydrogel.

Figure 24:
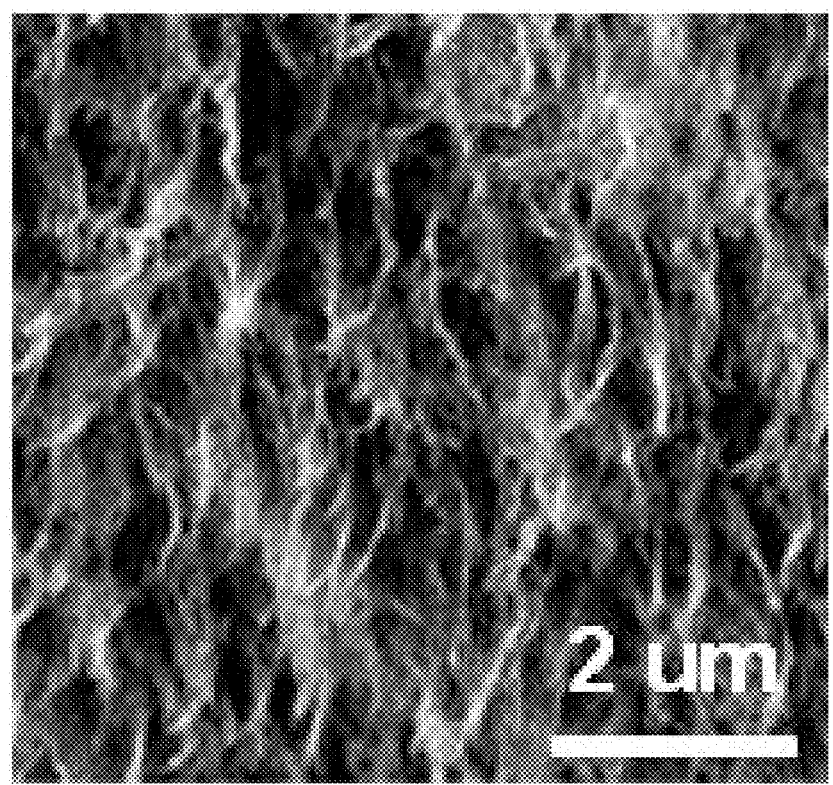
FIG. 24 is an SEM image of a hydrogel prepared with 16 wt. percent acrylamide, 5 wt. percent NIPAAm, and 8.234 wt. percent DSCG.

In a further aspect herein, for increasing the volume of catalytic reactions, materials having a large surface area with loaded proteins are provided. Decreasing the binding affinity of the polymer onto the DSCG droplets can increase coalescence of the droplets, and thus increase the propensity of forming a bicontinuous phase. For example, adding a more hydrophobic (still water soluble) poly-N-isopropylacrylamide (polyNIPAM) into the polyacrylamide gel introduces a structure that highly resembles the bicontinuous morphology. Reference is made to FIG. 24, which is an SEM imaged of a prepared gel with 16 wt. percent acrylamide, 5 wt. percent NIPAAm, and 8.234 wt. percent DSCG. This bicontinuous hydrogel provides enormous surface area that can be decorated with desired protein receptors or enzymes, and thus, this material has potential for improving or enabling a wide range of applications including biosensor development, protein purification, heterogeneous biocatalysis and 3-dimensional cell culture. It is also possible to provide a Protein A-laden bicontinuous hydrogels with an even larger surface area to improve the efficiency of IgG isolation.

Two complementary methods for modifying protein to reduce their aggregation in solution and increase their thermal stability against denaturation are provided herein. Products made herein include (i) A stable but highly reactive bioconjugate reagent based on squarate derivatives that can be used to modify proteins in aqueous solution, (ii) a novel organic reagent—disodium cromoglycate molecules—that can induce protein recrystallization in water and (iii) a new class of heterogeneous biocatalysts based on enzyme-laden porous hydrogel materials that can be used repeatedly to catalyze targeted organic reaction or synthesis of molecules of therapeutic interests. Methods provided herein include (i) a method (and new reagents) for modifying protein with non-natural sugar alcohols and (i) protein glycosylation wherein a highly active heterogeneous biocatalyst is used to glycosylate protein with targeted natural sugars. It is also possible to modify protein with more elaborate non-natural sugar alcohols including oligo-glycerol and oligo-alditols with stereochemical control.

Figure 25:
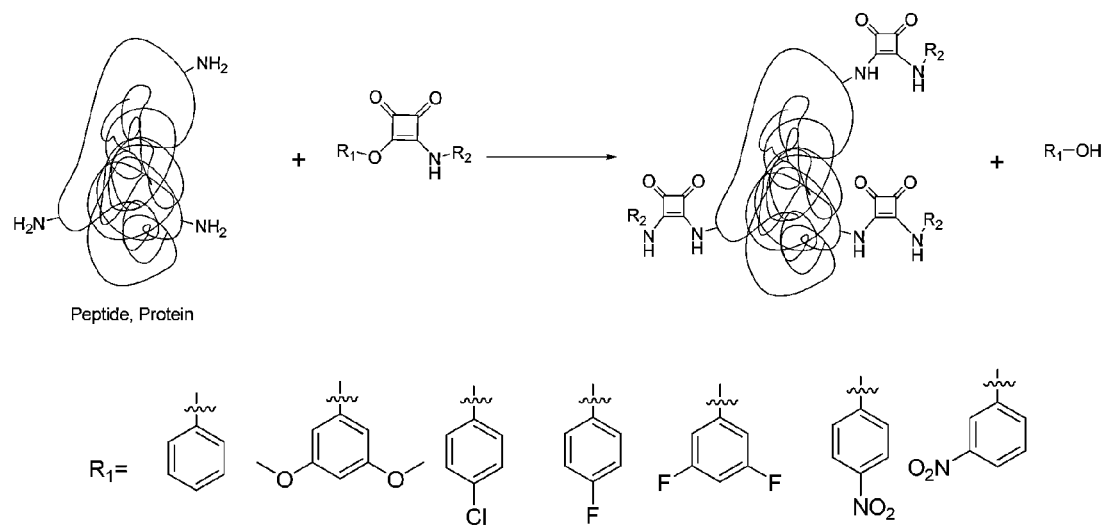
FIG. 25 is a schematic diagram of protein modification using amino squarate moiety, where $R_2$ can be a drug or a functional group that prevents protein aggregation.
Figure 26:
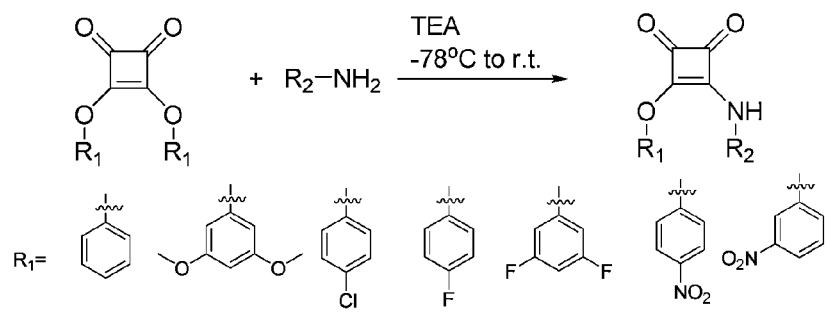
FIG. 26 is a schematic diagram of a general synthesis scheme for amino squarate reagents, where $R_2$ can be a drug or a functional group that prevents protein aggregation.

FIG. 25 shows an example of alternative embodiment of the new reaction recorded in FIG. 6. In particular, protein modification is performed using amino squarate moiety, where $R_2$ can be a drug or a functional group that prevents protein aggregation, and $R_1$ is different functional group that can make the reaction faster. The synthesis of the amino squarate reagents of FIG. 25 are set forth in FIG. 26.

Figure 27:
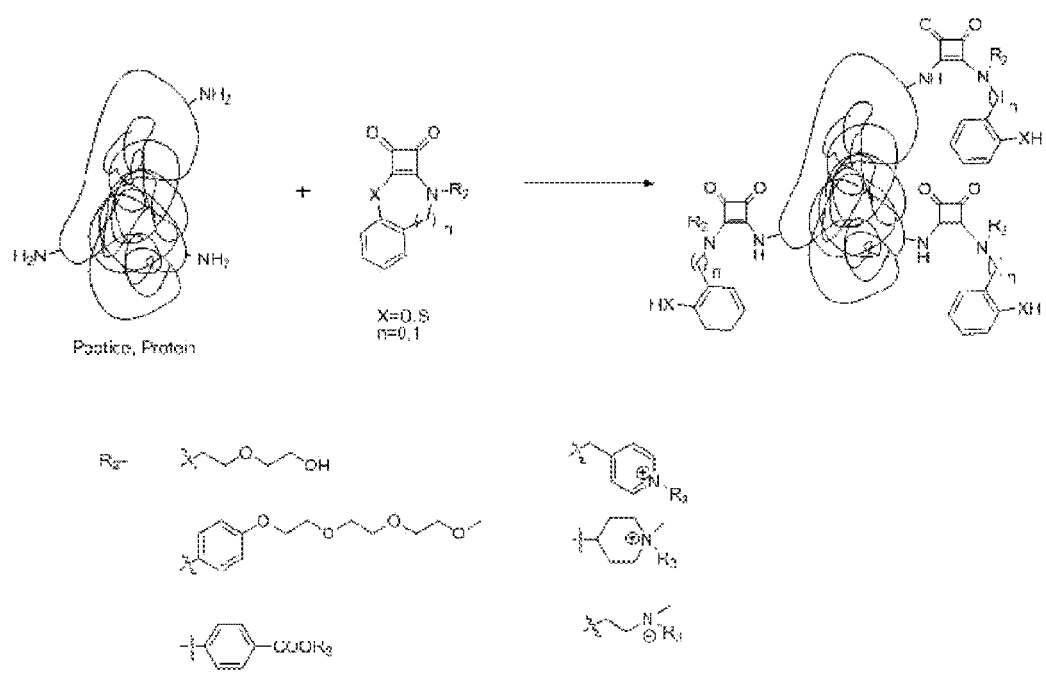
FIG. 27 is a schematic diagram of the cyclic version of amino squarate derivatives and the selected protein, where $R_3$ can be a drug or a functional group that prevents protein aggregation.
Figure 28:
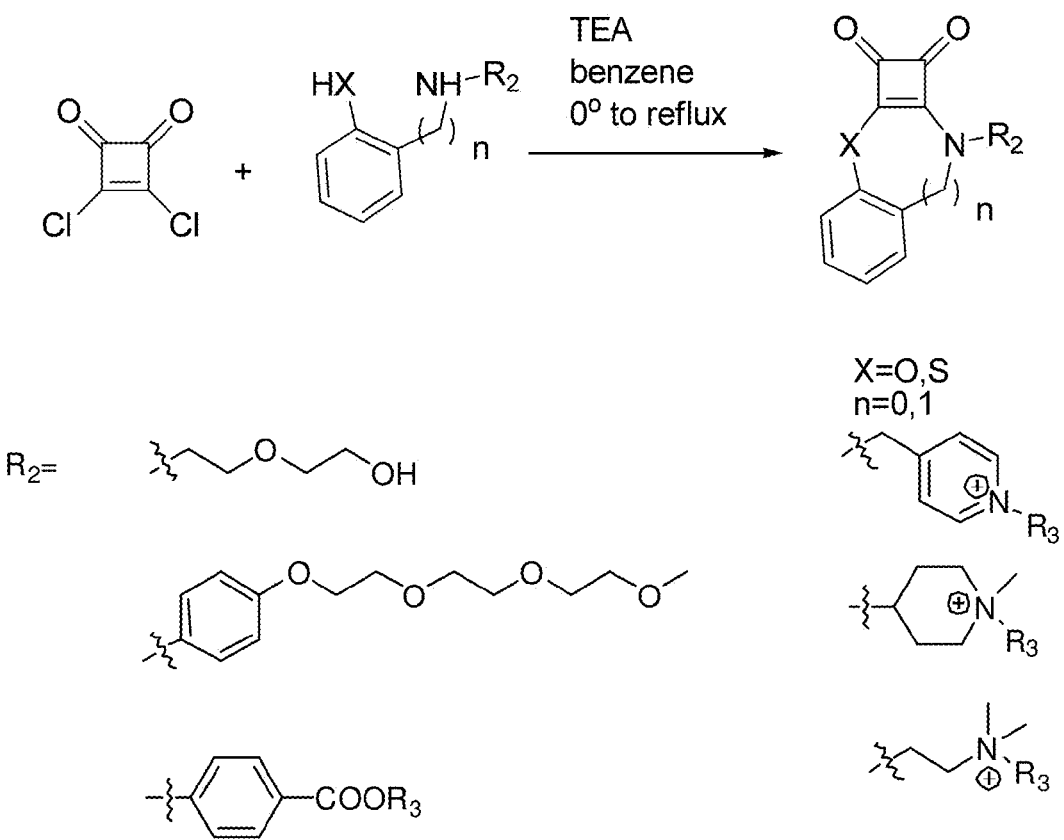
FIG. 28 is a schematic diagram of general synthesis scheme for cyclic amino squarate reagents, where $R_3$ can be a drug or a functional group that prevents protein aggregation.
Figure 29:
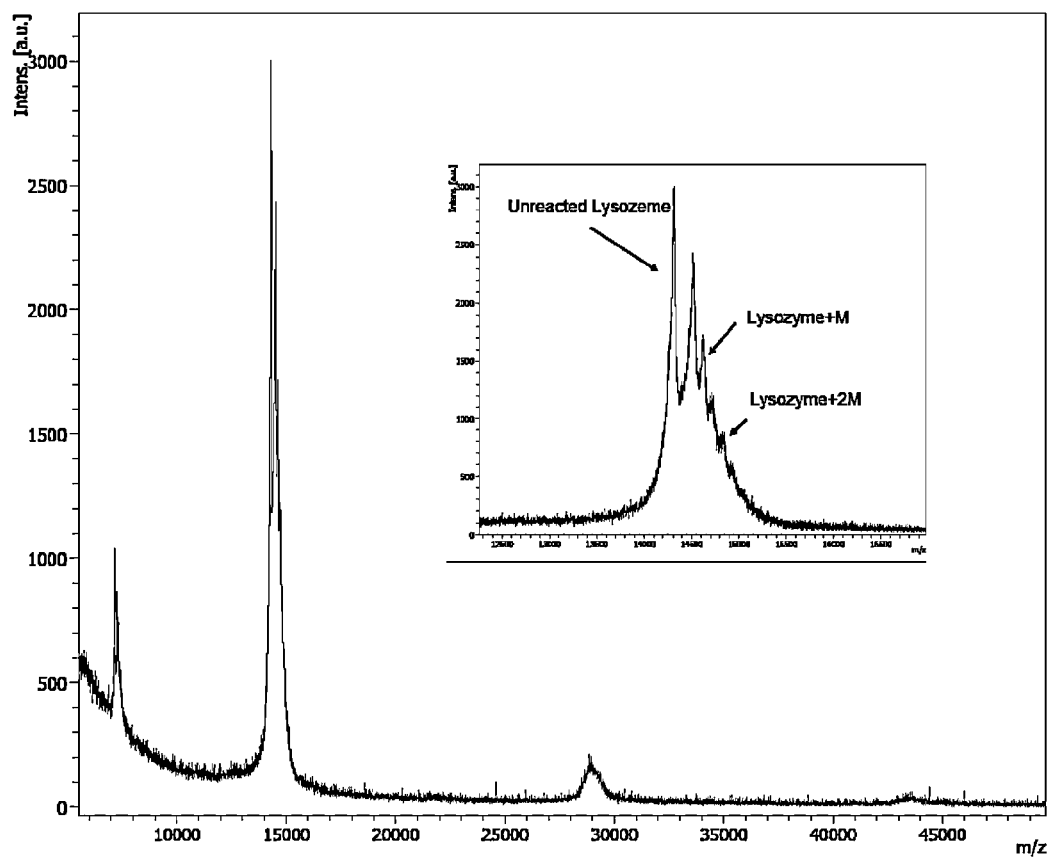
FIG. 29 is a spectragraph of MALDI-TOF indicating the modified proteins (lysozyme and carbonic anhydrase) with squarate groups (no-side-product bioconjugation method using cyclic version of squarate agent.
Figure 30:
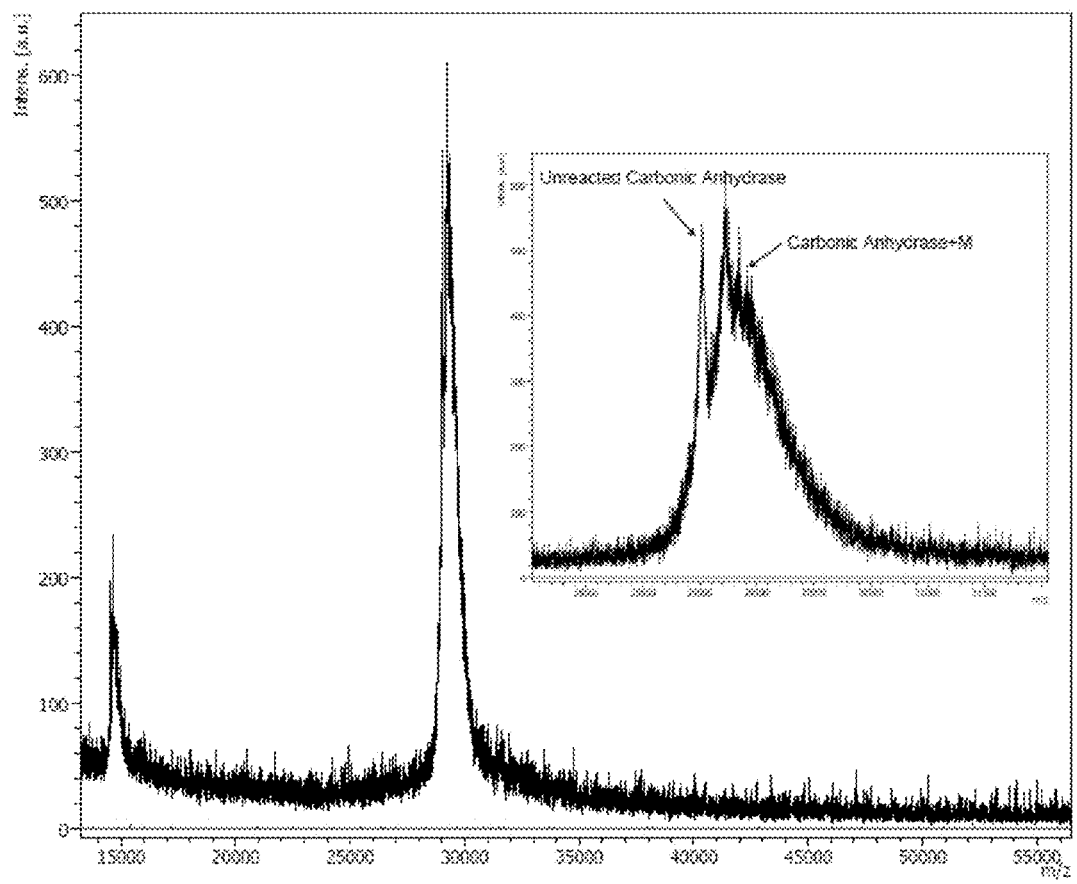
FIG. 30 is a spectragraph of MALDI-TOF indicating the modified proteins (lysozyme and carbonic anhydrase) with squarate groups (no-side-product bioconjugation method using cyclic version of squarate agent.

No-side-product bioconjugation method. Referring to FIG. 27, the invention of a cyclic version of the amino squarate derivatives and the selected protein may be combined. This cyclic amino squarate reagent modifies protein without side products. For example, lysozyme, carbonic anhydrase and BSA, were incubated in 10 mM PBS buffer at 28° C. for 5 hours to 3 days to give the desired modified protein at pH 7.28, 7.75, and 8.29 separately. $R_3$ can be a drug or a functional group that prevents protein aggregation. The modified proteins were characterized by MALDI-TOF, as discussed below. FIG. 28 is the general synthesis scheme for cyclic amino squarate reagents seen in FIG. 27, where $R_3$ represents a drug or a functional group that prevents protein aggregation. FIGS. 29 and 30 are a spectra of MALDI-TOF indicating the modified proteins (lysozyme and carbonic anhydrase) with squarate groups (no-side-product bioconjugation method using cyclic version of squarate agent.

Figure 31:
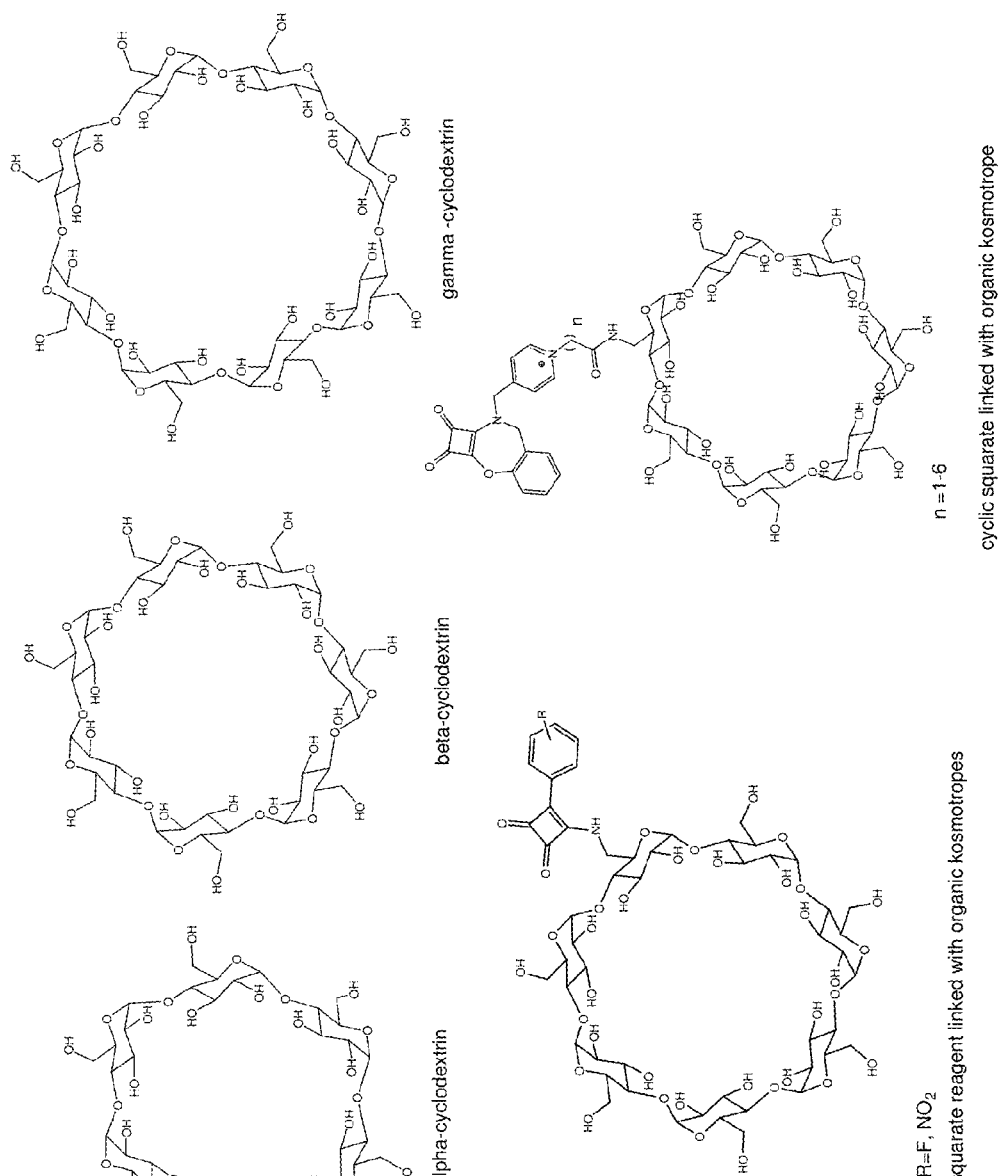
FIG. 31 is a schematic diagram of organic kosmotropes consisting of alpha-cyclodextrin, beta-cyclodextrin, gamma cyclodextrin; squarate reagent linked with organic kosmotropes; and cyclic squarate reagent linked with organic kosmotropes.
Figure 32:
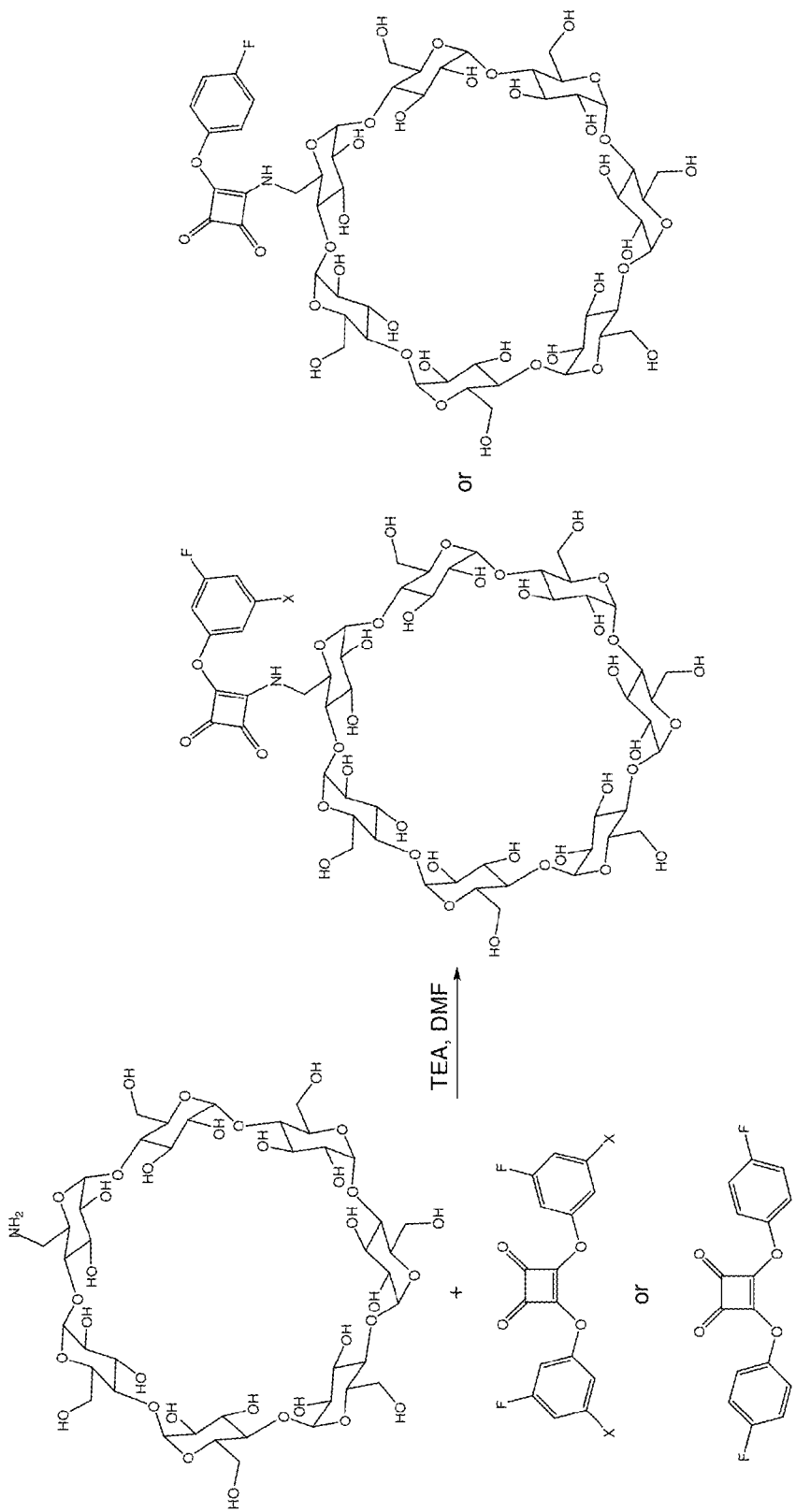
FIG. 32 is a schematic diagram of the reaction for linking the beta-cyclodextrin onto the amino squarate reagent.
Figure 33:
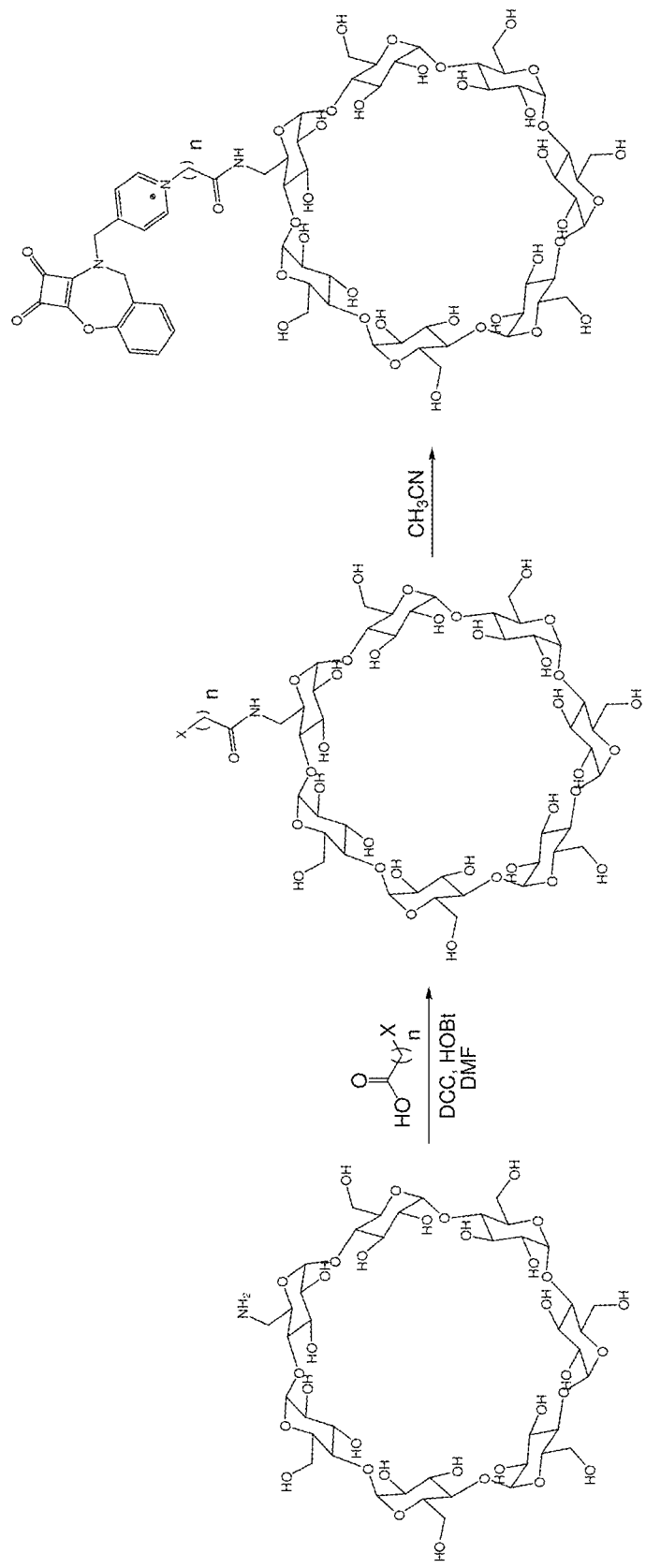
FIG. 33 is a schematic diagram of the reaction for linking the beta-cyclodextrin onto the cyclic amino squarate reagent.
Figure 34A:
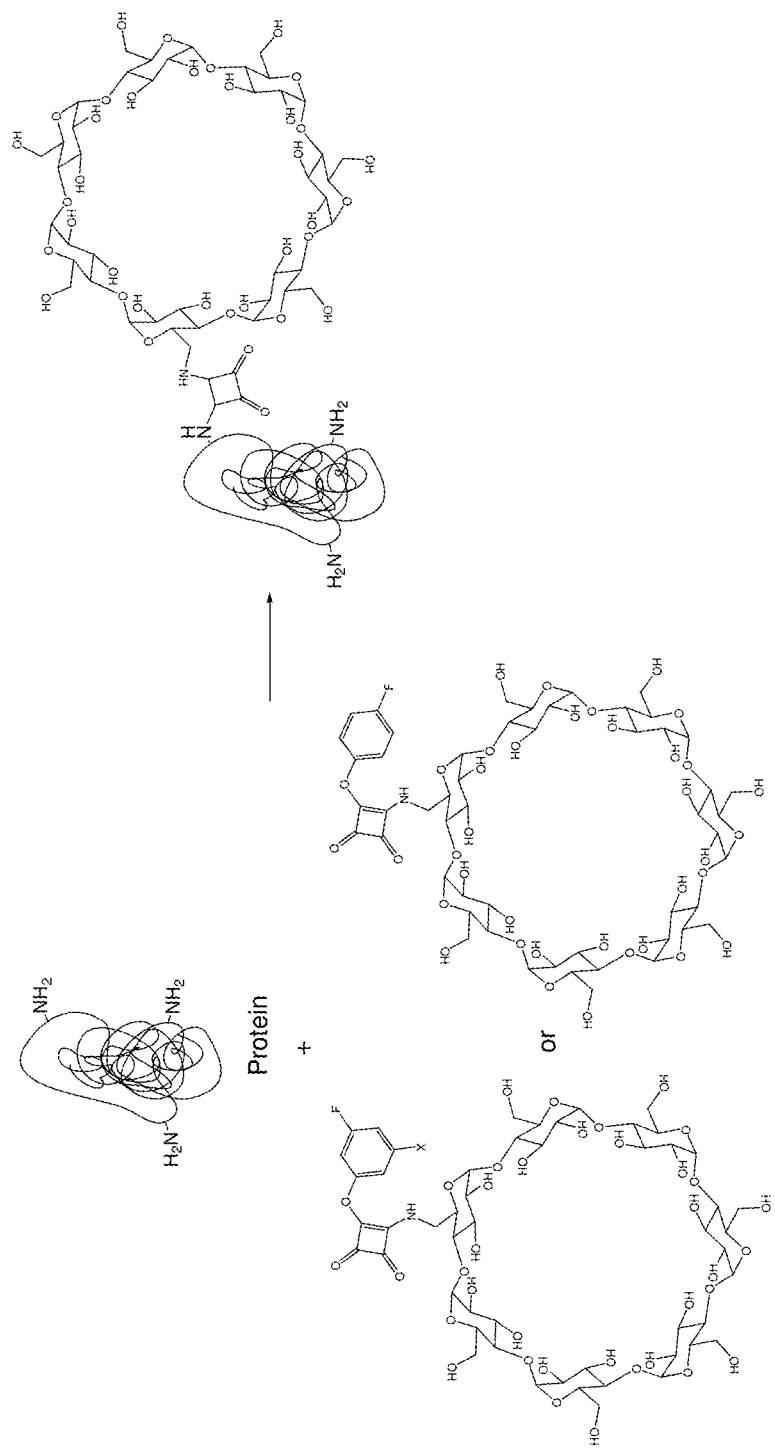
FIG. 34A is a schematic diagram of the first part of a scheme for modifying proteins with beta-cyclodextrin using amino squarate reagent or cyclic amino squarate reagent.
Figure 34B:
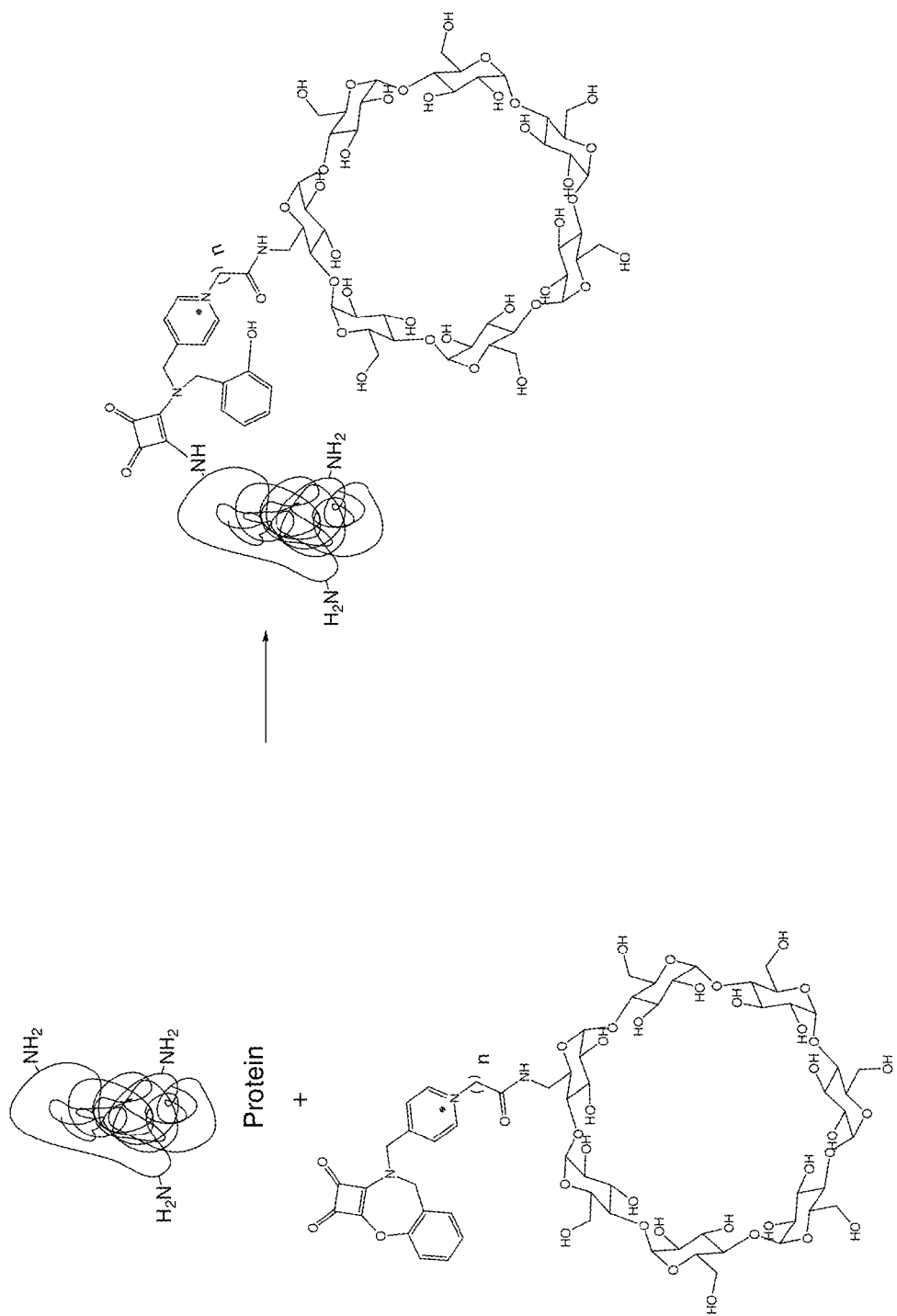
FIG. 34B is a schematic diagram of the second part of a scheme for modifying proteins with beta-cyclodextrin using amino squarate reagent or cyclic amino squarate reagent.
Figure 35:
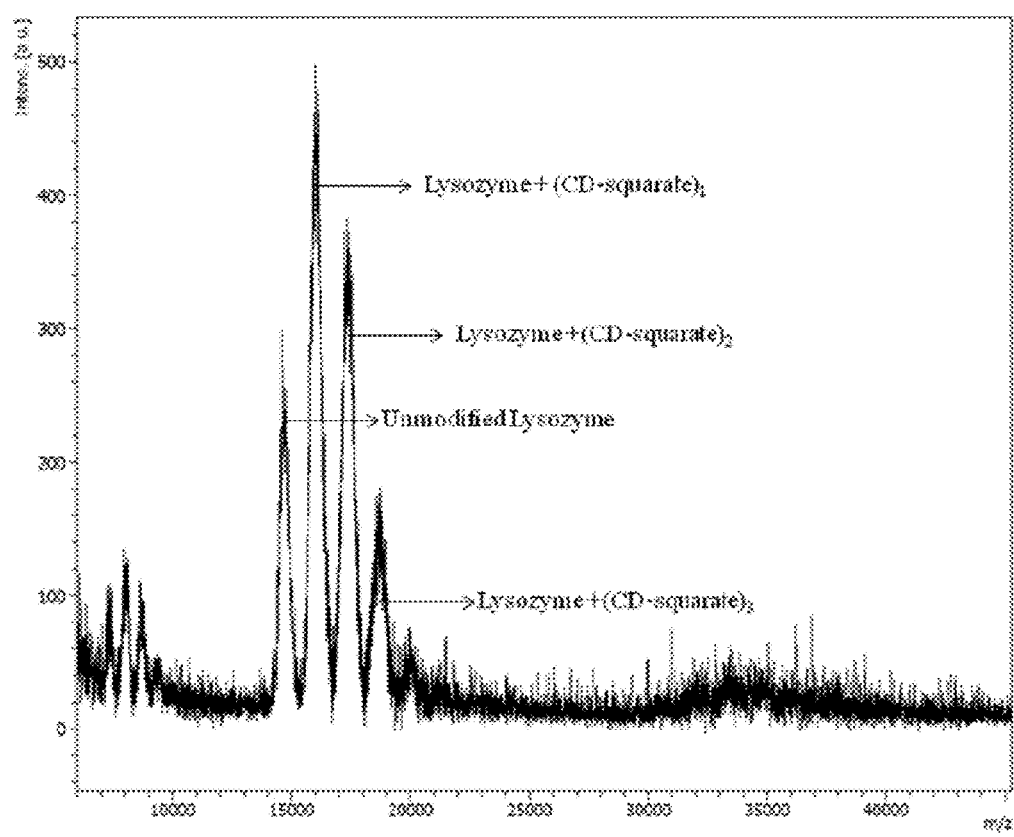
FIG. 35 is a spectragraph of MALDI-tof indicating the modified proteins (lysozyme) with beta-cyclodextrin using squarate linkage (using bioconjugation method shown in FIG. 25).

FIG. 31 illustrates another alternative embodiment of the basic system shown in FIG. 6 that uses a class of molecules called organic kosmotropes to tether to proteins to reduce protein aggregation and increase blood stream life (and thus enhanced activity). Two classes of organic kosmotropes are used: cyclodextrin and sugar alcohols. In particular, organic kosmotropes consisting of alpha-cyclodextrin, beta-cyclodextrin, gamma cyclodextrin may be linked with a squarate reagent or a cyclic squarate reagent. FIG. 32 illustrates a reaction for linking the beta-cyclodextrin onto a amino squarate reagent and FIG. 33 illustrates a reaction for linking the beta-cyclodextrin onto a cyclic amino squarate reagent. FIGS. 34A and 34B illustrate how the cyclodextrin are linked to the proteins by using amino squarate reagent or cyclic amino squarate reagent. FIG. 35 demonstrates the effectiveness of the reaction in that the proteins (in this example, lysozyme) has been modified with beta-cyclodextrin using squarate linkage (using bioconjugation method shown in FIG. 34A).

Figure 36:
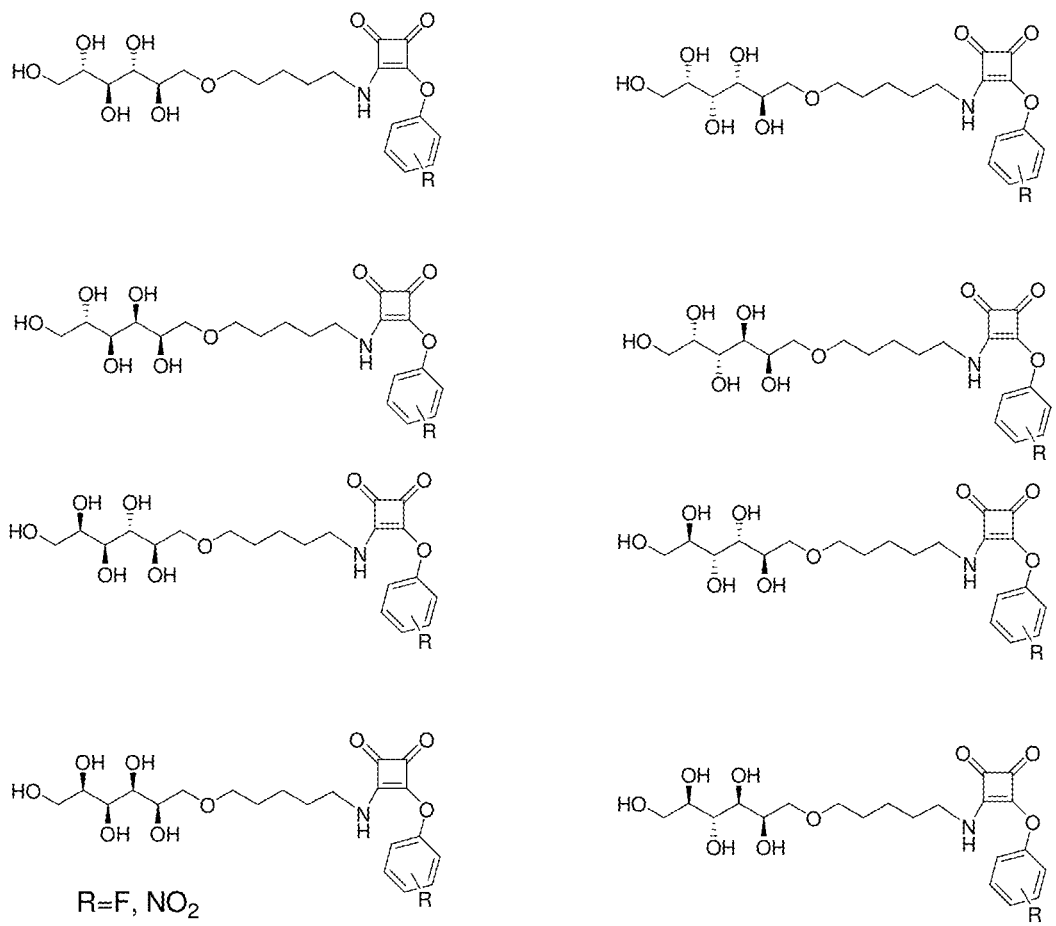
FIG. 36 is a schematic diagram of organic kosmotropes consisting of 8 sugar alcohols; squarate reagent linked with sugar alcohols; and cyclic squarate reagent linked with organic kosmotropes.
Figure 36:
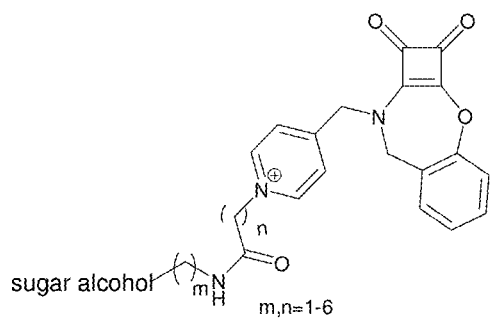
Figure 37:
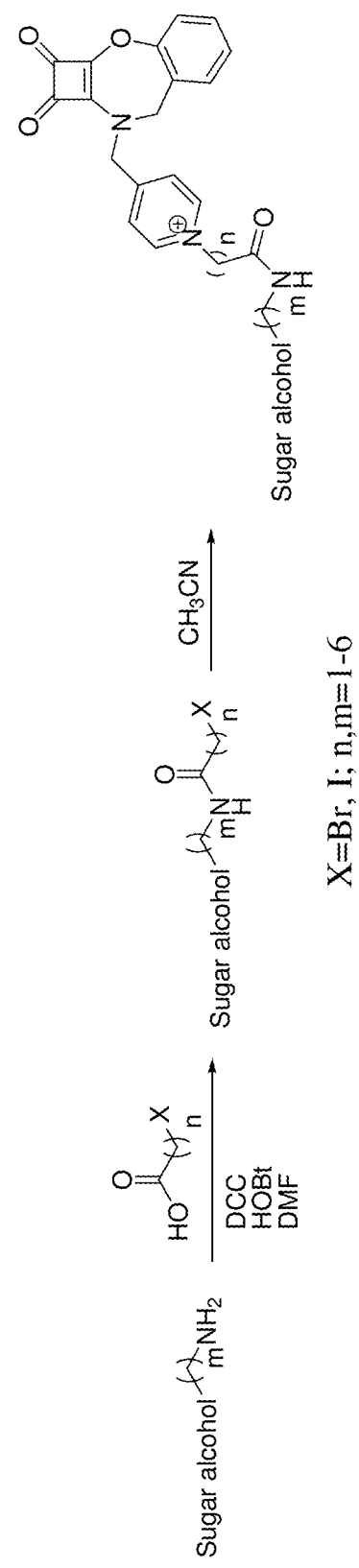
FIG. 37 is a schematic diagram of a reaction for linking the sugar alcohols onto the cyclic amino squarate reagent.
Figure 38:
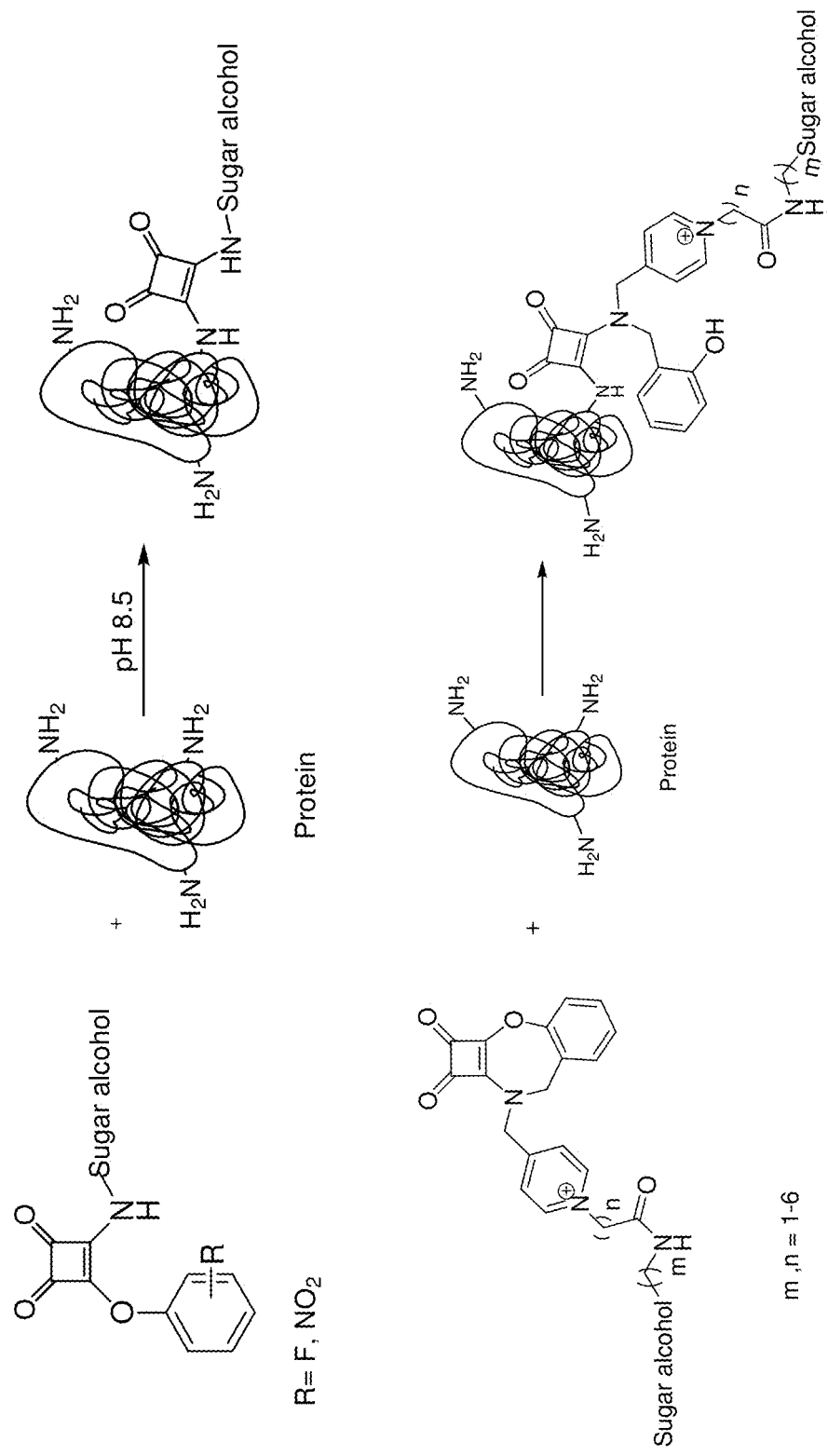
FIG. 38 is a schematic diagram of a scheme for modifying protein with sugar alcohol using amino squarate reagent or cyclic amino squarate reagent.

The present invention may also be employed in connection with organic kosmotropes consisting of eight sugar alcohols, shown individually and linked to a cyclic squarate in FIG. 36. The reaction for linking the sugar alcohols to the cyclic amino squarate reagent is shown in FIG. 37. The linked sugar alcohols and cyclic amino squarate reagent may then be used to modify a protein, as seen in FIG. 38.

Figure 39:
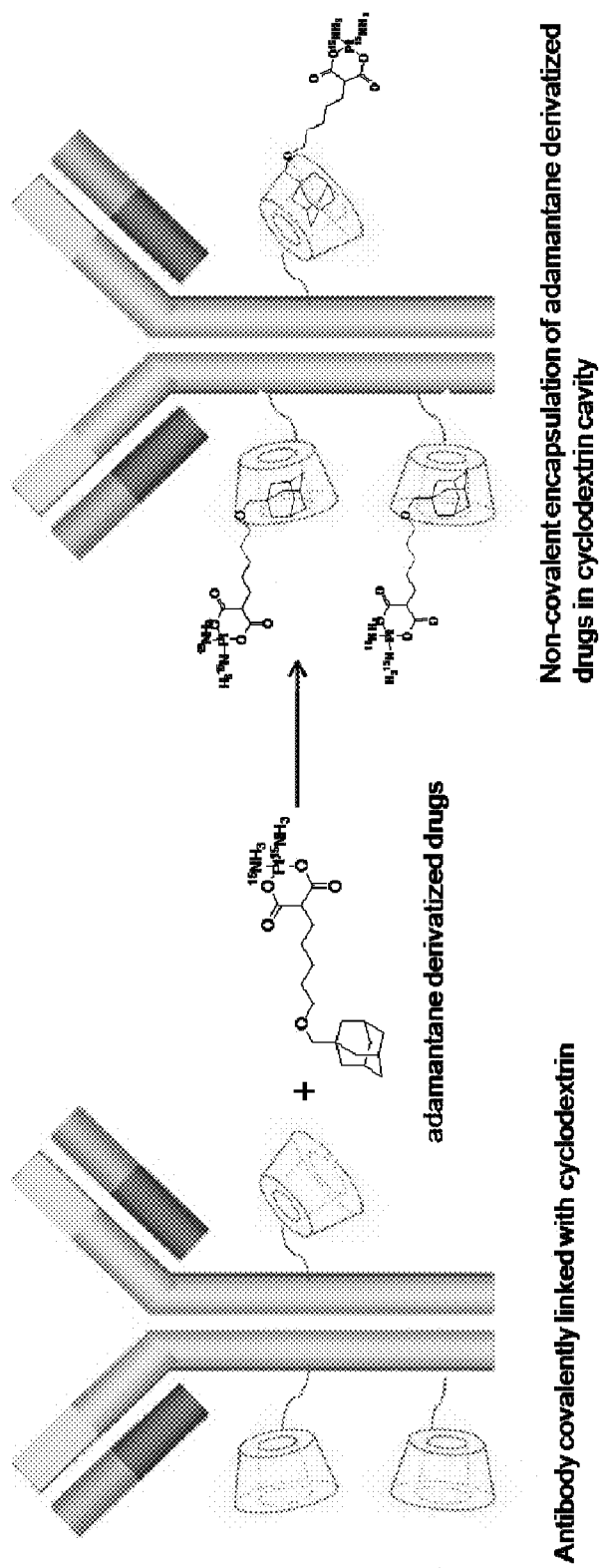
FIG. 39 is a schematic diagram of beta-cyclodextrin covalently linked with an antibody and loaded with small molecule drugs for target drug delivery.

The present invention may also be used to non-covalently load protein drugs, such as antibodies, with small molecule drugs for combined drug therapeutics. An example of beta-cyclodextrin covalently linked with an antibody and loaded with small molecule drugs for target drug delivery and/or combined drug therapeutics is shown in FIG. 39.

Figure 40:
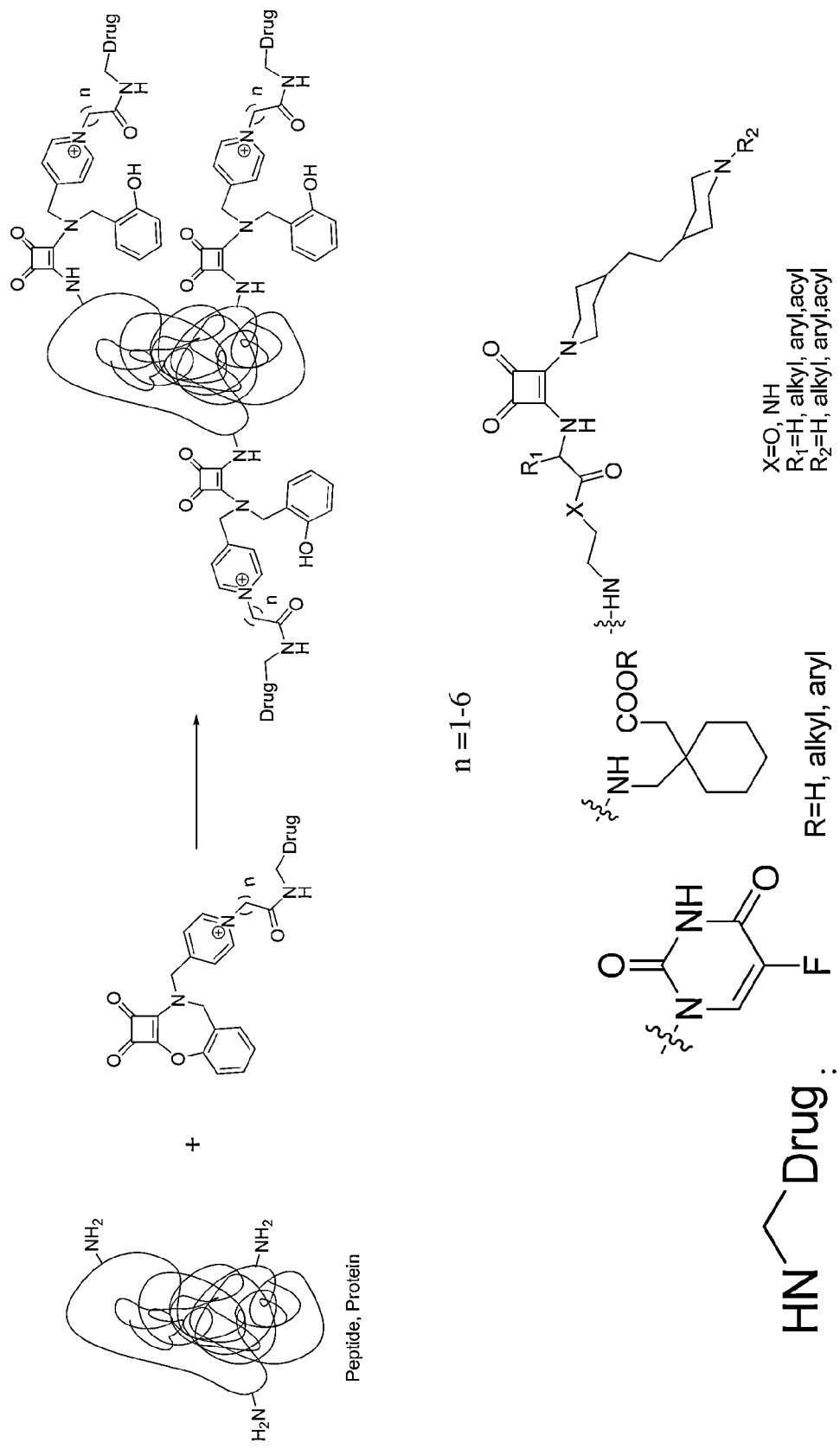
FIG. 40 is a schematic diagram of exemplary small molecule drugs on the cyclic amino squarate covalently linked with antibody for target drug delivery.
Figure 41:
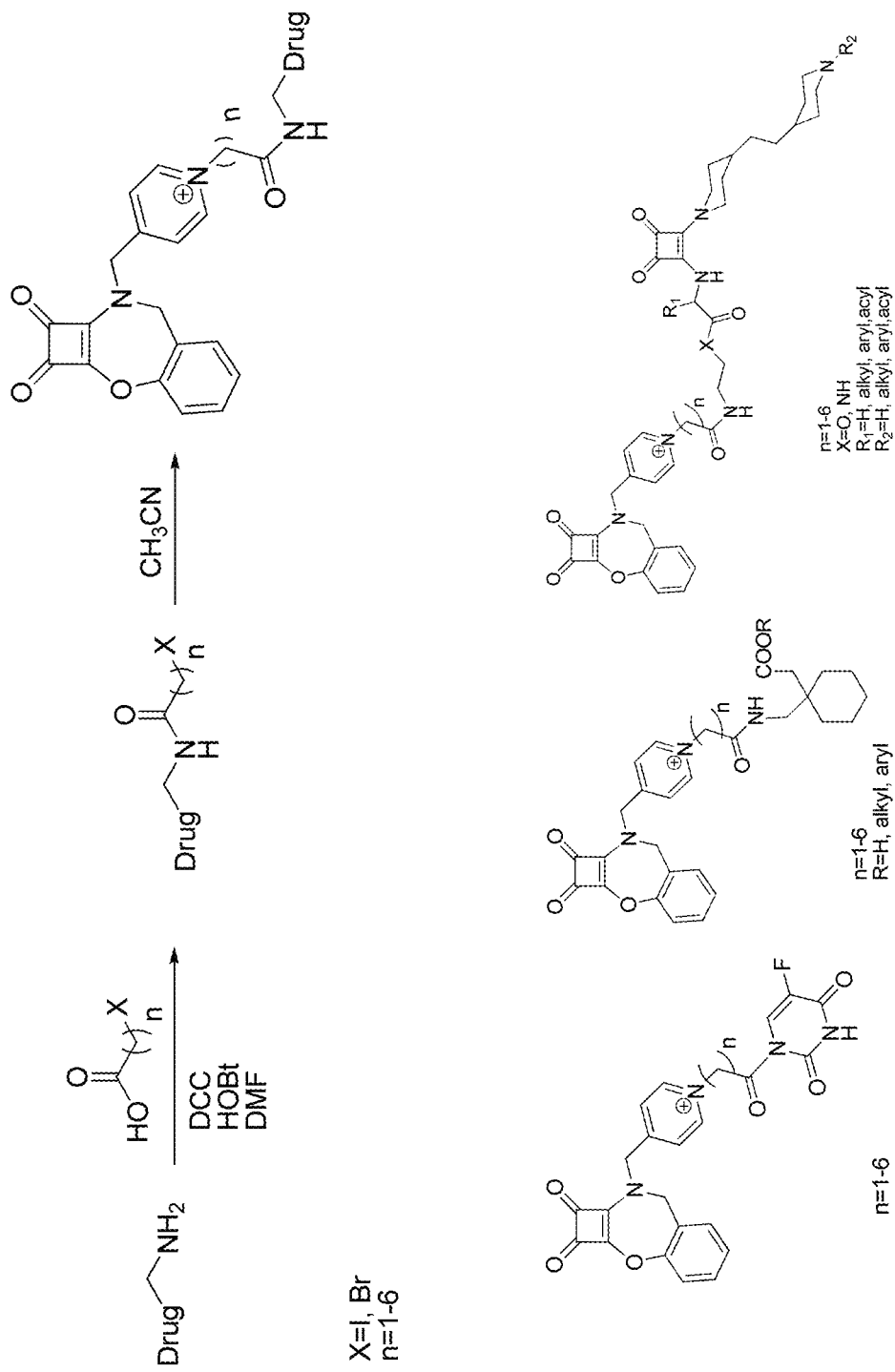
FIG. 41 is a schematic diagram of a general synthetic scheme for conjugating exemplary drugs to the cyclic amino squarate reagent.

The present invention may also be used to covalently modify protein drugs, such as antibodies, with small molecule drugs for combined drug therapeutics. For example, FIG. 40 illustrates various exemplary small molecule drugs conjugated on the cyclic amino squarate reagants, which are covalently linked to an antibody for targeted drug delivery and/or combined drug therapeutics. Along these lines, FIG. 41 illustrates a general synthetic scheme for conjugating exemplary drugs to the cyclic amino squarate reagent. Examples of drugs that a suitable for modification according to the present invention include Telfast, Diovan, Gaster, Imigran, Lupron, Neurontin, Plavix, Risperdal, Serevent, and Zyprexa.

What is claimed is:

1. A method of modifying a protein, comprising the step of covalently bonding said protein directly to a squarate molecule that is covalently bonded directly to an organic kosmotrope.

2. The method of claim 1, wherein said organic kosmotrope is a sugar alcohol.

3. The method of claim 1, wherein said organic kosmotrope is a cyclodextrin.

4. The method of claim 1, wherein the protein comprises a small molecule drug.

5. The method of claim 1, wherein the protein comprises an antibody.

6. The method of claim 3, wherein said cyclodextrin comprises alpha-cyclodextrin, beta-cyclodextrin, or gamma cyclodextrin.

7. The method of claim 1, wherein said squarate molecule is a cyclic squarate molecule.

8. A stabilized compound, comprising:
a protein; and
an organic kosmotrope covalently bonded to a squarate molecule that is covalently bonded to said protein.

9. The compound of claim 8, wherein said organic kosmotrope is a cyclodextrin.

10. The compound of claim 8, further comprising a squarate molecule.

11. The compound of claim 8, wherein the protein comprises a small molecule drug.

12. The compound of claim 8, wherein the protein comprises an antibody.

13. The compound of claim 9, wherein said cyclodextrin comprises alpha-cyclodextrin, beta-cyclodextrin, or gamma cyclodextrin.

14. The compound of claim 8, wherein said cyclodextrin is linked with a squarate molecule.

15. The compound of claim 14, wherein said squarate molecule is a cyclic squarate molecule.

* * * * *